US006875610B2

(12) United States Patent
Higginbotham et al.

(10) Patent No.: US 6,875,610 B2
(45) Date of Patent: Apr. 5, 2005

(54) METHODS AND COMPOSITIONS FOR EFFICIENT GENE TRANSFER USING TRANSCOMPLEMENTARY VECTORS

(75) Inventors: James N. Higginbotham, Ames, IA (US); Charles J. Link, Des Moines, IA (US); William J. Ramsey, Ames, IA (US)

(73) Assignee: Human Gene Therapy Research Institute, Des Moines, IA (US)

( * ) Notice: Subject to any disclaimer, the term of this patent is extended or adjusted under 35 U.S.C. 154(b) by 88 days.

(21) Appl. No.: 09/871,183

(22) Filed: May 31, 2001

(65) Prior Publication Data

US 2002/0042139 A1 Apr. 11, 2002

Related U.S. Application Data

(60) Provisional application No. 60/208,248, filed on May 31, 2000.

(51) Int. Cl.$^7$ ..................... C12N 15/861; C12N 15/63; C12N 15/64; C12N 5/10; C07H 21/04
(52) U.S. Cl. .................... 435/457; 435/320.1; 435/455; 435/456; 435/325; 435/69.1; 536/23.1; 536/23.5; 536/23.2; 536/23.7; 536/24.1
(58) Field of Search ............................ 435/320.1, 455, 435/456, 457, 325, 69.1; 536/23.1, 23.5, 23.2, 23.7, 24.1

(56) References Cited

U.S. PATENT DOCUMENTS

| | | | |
|---|---|---|---|
| 6,020,191 A | 2/2000 | Scaria et al. | |
| 6,083,750 A | 7/2000 | Chamberlain et al. | |
| 6,204,052 B1 | 3/2001 | Bout et al. | |
| 6,225,113 B1 | 5/2001 | Brough et al. | |
| 6,225,289 B1 | 5/2001 | Kovesdi et al. | |
| 6,228,646 B1 | 5/2001 | Hardy | |
| 2003/0096787 A1 * | 5/2003 | Perricaudet et al. | .......... 514/44 |

FOREIGN PATENT DOCUMENTS

| | | |
|---|---|---|
| EP | 1 059 356 | 12/2000 |
| WO | WO 98/22143 | 5/1998 |
| WO | WO 99/46371 | 9/1999 |
| WO | WO/00/17376 | 3/2000 |

OTHER PUBLICATIONS

Salmons et al., Human Gene Therapy, 1993, vol. 4, pp. 129–141.*
Bridge, Eileen, et al., "Adenovirus Early Region 4 and DNA Synthesis", Dec. 21, 1992, Virology 193, 794–801 (1993).
Graham, Frank L., et al., "Defective Transforming Capacity of Adenovirus Type 5 Host–Range Mutants", Nov. 28, 1977, Virology 86, 10–21 (1978).
Ramsey, W. Jay, et al., "Adenovirus Vectors as Transcomplementing Templates for the Production of Replication Defective Retroviral Vectors", May 1, 1998, Biochemical and Biophysical Research Communications 246, 912–919 (1998).

Alemany, et al., "Complementary adenoviral vectors for oncolysis", Cancer Gene Therapy 6(1):21–25 (1999).
Bischoff, et al., "An Adenovirus Mutant That Replicates Selectively in p53–Deficient Human Tumor Cells", Science 274:373–376 (1996).
Caplen, et al., "Adeno–retroviral chimeric viruses as in vivo transducing agents", Gene Therapy 6:454–459 (1999).
Wildner, et al., "Adenoviral vectors capable of replication improve the efficacy of HSVk/GCV suicide gene therapy of cancer", Gene Therapy 6:57–62 (1999).
Cossel, "A New Avian Leukosis Virus–Based Packaging Cell line That Uses Two Separate Transcomplementing Helper Genomes," Virology, vol. 64, (No. 3,) pp. 1070–01078, (1990).
Dion, "Quantitative And In Vivo Activity Of Adenoviral–Producing Cells Made By Cotransduction Of A Replication–Defective Adenovirus And A Replication–Enabling Plasmid," Cancer Gene Therapy, vol. 3, (No. 4,) pp. 230–237, (1996).
Ditzhuijzen, "Benefits From The Automation Of A Rolling Mill," Steel Times International, 13 , (No. 5,) pp. 36–38, (1989).
Feng, "Stable In Vivo Gene Transduction Via A Novel Adenoviral/Retroviral Chimeric Vector," Nature Biotechnology vol. 15, pp. 866–870 (Sep. 1997).
Kemer, "Complementation Of Adenovirus E4 Mutants By Transient Expression Of E4 cDNA And Deletion Plasmids," Nucleic Acids Research, vol. 17, (No. 8,) pp. 3037–3048, (1989).
Lanuti, "Evaluation Of An E1E4–Deleted Adenovirus Expressing The Herpes Simplex Thymidine Kinase Suicide Gene In Cancer Gene Therapy," Human Gene Therapy, vol. 10, pp. 463–475, (Feb. 1999).
Mandell, "Gene Therapy Of Cancer By Retroviral Transfer And Expression Of The Rat Sodium/Iodide Symporter (NIS)" Proceedings Of The Annual Meeting Of The American Association For Cancer Research, vol. 38. (No. 1,) p. 381, (Mar. 1997).
Noguiez–Hellin, "Generation Of A Transcomplementable Defective Recombinant Provirus Transducing A Foreign Gene," Medical Sciences, vol. 319, pp. 45–50, (1996).
Okada, "Efficient Directional Cloning Of Recombinant Adenovirus Vectors Using DNA–Protein Complex," Nucleic Acids Research, vol. 26, (No. 8,) pp. 1947–1950.

* cited by examiner

Primary Examiner—David Guzo
(74) Attorney, Agent, or Firm—McKee, Voorhees & Sease, P.L.C.

(57) ABSTRACT

The invention includes a viral vector method and composition comprising transcomplementary replication incompetent viral vectors, preferably adenoviral vectors, which are cotransformed to a recipient cell. The two vectors complement each other and thus allow viral replication, in a synergistic combination which enhances both gene delivery and gene expression of genetic sequences contained within the vector.

8 Claims, 25 Drawing Sheets

(4 of 25 Drawing Sheet(s) Filed in Color)

Basic Wild Type Adenovirus Genome

Ad Vector #1

+

Ad Vector #2

Ad Vector #1

+

Ad Vector #2

Improved Delivery using Tumor Restricted Replication

METHODS AND COMPOSITIONS FOR EFFICIENT GENE TRANSFER USING TRANSCOMPLEMENTARY VECTORS

CROSS REFERENCE TO RELATED APPLICATION

This application claims priority to commonly owned U.S. provisional application Ser. No. 60/208,248 filed May 31, 2000 entitled DUAL ADENOVIRAL DELIVERY OF TRANSGENES. Priority is claimed under 35 U.S.C. section 119(e).

FIELD OF THE INVENTION

This invention relates generally to genetic engineering and more specifically to improvements in components and methods used in genetic engineering, namely vectors. Vectors produced by the teachings herein can be used in any of a number of molecular protocols including in vitro, ex vivo or in vivo modification of nucleotide sequences present in cells.

BACKGROUND OF THE INVENTION

The field of gene therapy has made significant gains in recent years. The combination of genetic defects being identified and gene target/delivery methods being developed has led to an explosion in the number of clinical gene therapy protocols. The central focus of gene therapy is to develop methods for introducing new genetic material into somatic cells. To date two general classes of gene transfer methods have evolved. The first is DNA-mediated gene transfer and involves direct administration of DNA to the patient in various formulations. These methods use genes as medicines in a manner much like conventional organic or protein compounds. DNA-mediated gene transfer however has proven quite difficult. Methodology such as microinjection, lipofection, and receptor mediated endocytosis have usually resulted in lower gene transfer, and have usually established only transient residence of the novel gene in the targeted cell. Permanent incorporation of genes into cells occurs rarely after DNA-mediated gene transfer in cultured cells (less than $1 \times 10^5$ cells) and has not been significantly observed in vivo. Thus DNA-mediated gene transfer may be inherently limited to the use of genes as medicines that are administered by conventional parenteral routes to provide a therapeutic effect over predictable period of time. Studies of a therapeutic gene product may be constituted by repetitively dosing the patient with degenerate material much like conventional pharmaceutical medicines.

Viral gene transfer on the other hand involves construction of synthetic virus particles (vectors) that lack pathogenic functions. The virus particles are incapable of replication and contain a therapeutic or diagnostic gene within the viral genome which is delivered to cells by the process of infection. To date the viral vector which has achieved the most success is the retroviral vector. The prototype for a retroviral mediated gene transfer is a retroviral vector derived from Moloney Murine Leukemia Virus. Retroviral vectors have several properties that make them useful for gene therapy. First is the ability to construct a "defective" virus particle that contains the therapeutic gene and is capable of infecting cells but lacks viral genes and expresses no viral gene products which helps to minimize host response to potential viral epitopes.

Retroviral vectors are capable of permanently integrating the genes they carry into the chromosomes of the target cell. Considerable experience in animal models and initial experience in clinical trials suggest that these vectors have a high margin of safety.

Vectors based on adenovirus have recently proven effective as vehicles for gene transfer in vitro and in vivo in several cell types. Adenoviral vectors are constructed using a deleted adenoviral genome that lacks either the e-3, e-4 or gene region and/or the e-1 gene region that is required for producing a replicating adenovirus particle. Recombinant genes are inserted into the site of the deleted gene region(s). Adenoviral particles are then produced in a cell line that is able to express e-1, e-4 or e-3 genes and thus capable of assembling a viral particle which contains only the recombinant viral genome with the therapeutic gene.

Adenoviral vectors differ from retroviral vectors in that they do not integrate their genes into the target cell chromosome. Adenoviral vectors will infect a wide variety of both dividing and non-dividing cells in vitro and in vivo with a high level of efficiency providing expression of their recombinant gene for a period of several weeks to months.

Current technology has enabled construction of adenoviral vectors that are incapable of proliferating however they are not completely "defective" and will express a series of viral gene products which can generate host immune response to the viral epitopes presented causing quick elimination of the already transient vector.

Adenovirus is a non-enveloped, nuclear DNA virus with a genome of about 36 kb, which has been well-characterized through studies in classical genetics and molecular biology (Horwitz, M. S., "Adenoviridae and Their Replication," in Virology, $2^{nd}$ ed., Fields et al., eds., Raven Press, New York 1990). The viral genes are classified into early (known as E1–E4) and late (known as L1–L5) transcriptional units, referring to the generation of two temporal classes of viral proteins. The demarcation between these events is viral DNA replication.

Recombinant adenoviruses have several advantages for use as gene transfer vectors, including tropism for both dividing and non-diving cells, minimal pathogenic potential, ability to replicate to high titer for preparation of vector stocks, and the potential to carry large inserts (Berkner, K. L., Curr. Top. Micro. Immunol. 158:39–66, 1992; Jolly, D., Cancer Gene Ther. 1:51–64, 1994).

The cloning capacity of an adenoviral vector is proportional to the size of the adenovirus genome present in the vector. For example, a cloning capacity of about 8 kb can be created from the deletion of certain regions of the virus genome dispensable for virus growth, e.g., E3, and the deletion of a genomic region such as E1 whose function may be restored in trans from 293 cells (Graham, F. L., J. Gen. Virol. 36:59–72, 1977) or A549 cells (Imler et al., Gene Ther. 3:75–84, 1996). Such E1-deleted vectors are rendered replication-defective. The upper limit of vector DNA capacity is about 105%–108% of the length of the wild-type genome. Further adenovirus genomic modifications are possible in vector design using cell lines which supply other viral gene products in trans, e.g., complementation of E2 (Zhou et al., J. Virol. 70:7030–7038, 1996), complementation of E4 (Krougliak et al, Hum. Gene Ther. 6:1575–1586, 1995). Maximum carrying capacity can be achieved using adenoviral vectors deleted for all viral coding sequences (Kochanek et al., Proc. Natl. Acad. Sci. USA 93:5731–5736, 1996; Fisher et al., Virology 217:11–22, 1996).

Transgenes that have been expressed to date by adenoviral vectors include p53 (Wills et al., Hum. Gene Ther. 5:1079–188, 1994); dystrophin (Vincent et al., Nature Genetics 5:130–134, 1993; erythropoietin (Descamps et al., Hum. Gene Ther. 5:979–985, 1994; omithine transcarbamylase (Stratford-Perricaudet et al., Hum. Gene Ther. 1:241–256, 1990; We et al., J. Biol. Chem. 271:3639–3646, 1996); adenosine deaminase (Mitani et al., Hum. Gene Ther. 5:941–948, 1994); interleukin-2 (Haddada et al., Hum. Gene Ther. 4:703–711, 1993); and α1-antitrypsin (Jaffe et al., Nature Genetics 1:372–378, 1992); thrombopoictin (Ohwada et al., Blood 88:778–784, 1996); and cytosine deaminase (Ohwada et al., Hum. Gene Ther. 7:1567–1576, 1996).

The tropism of adenoviruses for cells of the respiratory tract has particular relevance to the use of adenovirus in Gene Ther. for cystic fibrosis (CF), which is the most common autosomal recessive disease in Caucasians. Mutations in the cystic fibrosis transmembrane conductance regulator (CFTR) gene that disturb the cAMP-regulated Cl- channel in airway epithelia result in pulmonary dysfunction (Zabner et al., Nature Genetics 6:75–83, 1994). Adenoviral vectors engineered to carry the CFTR gene have been developed (Rich et al., Hum. Gene Ther. 4:461–476, 1993) and studies have shown the ability of these vectors to deliver CFTR to nasal epithelia of CF patients (Zabner et al., Cell 75:207–216, 1993), the airway epithelia of cotton rats and primates (Zabner et al., Nature Genetics 6:L75–83, 1994), and the respiratory epithelium of CF patients (Crystal et al., Nature Genetics 8:42–51, 1994). Recent studies have shown that administering an adenoviral vector containing a DNA sequence encoding CFTR to airway epithelial cells of CF patients can restore a functioning chloride ion channel in the treated epithelial cells (Zabner et al., J. Clin. Invest. 97:1504–1511, 1996).

Modifications to the adenovirus genomic sequences contained in the recombinant vector have been attempted in order to decrease the host immune response (Yang et al., Nature Genetics 7:362–369, 1994; Lieber et al., J. Virol. 70:8944–8960, 1996; Gorziglia et al., J. Virol. 70:4173–4178; Kochanek et al., Proc. Natl. Acad. Sci. USA 93:5731–5736, 1996; Fisher et al., Virology 217:11–22, 1996).

In addition to deletions in the adenovirus El region, first-generation adenoviral vectors often contain modifications to the E3 region in order to increase the packaging capacity of the vectors and to reduce viral gene expression (Yang et al., J. Virol. 69:2004–2015, 1995; Zsengeller et al., Hum. Gene Ther. 6:457–467, 1995; Brody et al., Hum. Gene Ther. 5:821–836, 1994). However, the adenovirus E3 regions contains certain proteins which modulate the host's antiviral immune response. The E3 transcription unit encodes the 12.5K, 6.7K, gp19K, 11.6K, 10.4K, 14.5K and 14.7K proteins (Wold et al., Trends Microbiol. 2:437–443, 1994). The E3 14.7K, 14.5K, and 10.4K proteins are able to protect infected cells from TNF-induced cytolysis. The adenovirus E3 gp19K protein can complex with MHC Class 1 antigens and retain them in the endoplasmic reticulum, which prevents cell surface presentation and killing of infected cells by cytotoxic T-lymphocytes (CTLs) (Wold et al., Trends Microbiol. 437–443, 1994), suggesting that its presence in a recombinant adenoviral vector may be beneficial. The E3 11.6K gene (Adenovirus death protein) is required for cell lysis and the release of adenovirus from infected cells (Tollefson et al., J. Virol. 70:2296–2306, 1996; Tollefson et al., Virology 220:152–162, 1996).

Earlier designs of adenoviral vectors in which the E3 region was modified have shown only transient expression of a transgene in the lungs of test animals (Yang et al., J. Virol. 69:2004–2015; Zsengeller et al., Hum Gene Ther. 6:457–467, 1995).

Modifications to the adenovirus E4 region have been introduced into adenoviral vectors in order to reduce viral gene expression and to further increase carrying capacity (Armentano et al., Hum. Gene Ther. 6:1343–1353, 1995). However, experiments in which adenoviral vectors were introduced into nude mice demonstrated that the context of the adenovirus E4 genomic region was a determinant in the persistence of expression, especially when the CMV promoter was used to control expression of the transgene (Kaplan et al., Hum. Gene Ther. 8:45–56, 1997; Armentano et al., J. Virol. 71:2408–2416, 1997).

The current state of adenoviral vector as well as viral vector based gene delivery requires the development of novel adenoviral vectors which demonstrate a capability for persistence and sustained expression of a transgene.

SUMMARY OF THE INVENTION

The following invention involves methods and strategies for improving efficiency of gene transfer of vectors. According to the invention, it has been discovered that a synergistic combination of cotranscomplementary replication defective vectors achieves gene transfer at increased levels as high as 13 fold.

The invention includes a viral vector method and composition comprising two transcomplementary replication incompetent adenoviral vectors which are transduced to a recipient cell. The two vectors complement each other in trans and thus allow viral replication, in a synergistic combination which enhances both gene delivery and gene expression of genetic sequences contain within the vector. The combination of the two vectors in vivo, demonstrated tumor reduction in mice as high as 100%. Any replication incompetent viral vector may be used according to the invention including but not limited to retroviral vectors, adenoviral vectors, adeno-associated viral vectors, lentivirus vectors (human and other including porcine), Herpes virus vectors, Epstein-Ban virus vectors, SV40 virus vectors, pox virus vectors, pseudotype virus vectors.

A first vector is engineered and/or introduced to be replication deficient. A second vector is also engineered and/or introduced which will complement in trans the first vector providing for viral replication after transduction in recipient cells.

The invention comprises a transformation composition comprising a mixture of the two or more vectors, methods of transformation using this combination, and genetic engineering protocols which take advantage of this high gene transfer and expression efficiency to transform recipient host cells with exogenous nucleotide sequences.

General transformation techniques including construction and use of vectors, are all known to those of skill in the art, are generally described herein, and are also described in the references disclosed and incorporated herein.

Definitions

Unless defined otherwise, all technical and scientific terms used herein have the same meaning as commonly understood by one of ordinary skill in the art to which this invention belongs. Generally, the nomenclature used herein and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document. Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). As employed throughout the disclosure, the following terms, unless otherwise indicated, shall be understood to have the following meanings and are more fully defined by reference to the specification as a whole:

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "assay marker" or "reporter" refers to a gene product that can be detected in experimental assay protocol, such as marker enzymes, antigens, amino acid sequence markers, cellular phenotypic markers, nucleic acid sequence markers, and the like.

The term "assaying for the expression" of a protein coding sequence means any test or series of tests that permits cells expressing the protein to be distinguished from those that do not express the protein. Such tests include biochemical and biological tests and use either "selectable markers" or "assay markers."

As used herein, "chromosomal region" includes reference to a length of a chromosome that may be measured by reference to the linear segment of DNA that it comprises. The chromosomal region can be defined by reference to two unique DNA sequences, i.e., markers.

A "cloning vector" is a DNA molecule such as a plasmid, cosmid, or bacterial phage that has the capability of replicating autonomously in a host cell. Cloning vectors typically contain one or a small number of restriction endonuclease recognition sites at which foreign DNA sequences can be inserted in a determinable fashion without loss of essential biological function of the vector, as well as a selectable marker gene that is suitable for use in the identification and selection of cells transformed with the cloning vector. Selectable marker genes typically include genes that provide tetracycline resistance or ampicillin resistance.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum,* or the ciliate *Macronucleus,* may be used when the nucleic acid is expressed therein.

When the nucleic acid is prepared or altered synthetically, advantage can be taken of known codon preferences of the intended host where the nucleic acid is to be expressed.

An "expression vector" is a DNA molecule comprising a gene that is expressed in a host cell. Typically, gene expression is placed under the control of certain regulatory elements including promoters, tissue specific regulatory elements, and enhancers. Such a gene is said to be "operably linked to" the regulatory elements.

The term "expression cassette" is used herein to refer to a genetic sequence which includes a protein encoding region which is operably linked to all of the genetic signals necessary to achieve expression of the protein encoding region. Traditionally, the expression system will include a regulatory element such as a promoter or enhancer, to increase transcription and/or translation of the protein encoding region, or to provide control over expression. The regulatory element may be located upstream or downstream of the protein encoding region, or may be located at an intron (noncoding portion) interrupting the protein encoding region. Alternatively it is also possible for the sequence of the protein encoding region itself to comprise regulatory ability.

The term "functional equivalent" refers to any derivative which is functionally substantially similar to the referenced sequence or protein. In particular the term "functional equivalent" includes derivatives in which nucleotide base(s) and/or amino acid(s) have been added, deleted or replaced without a significantly adverse effect on biological function and which will hybridize under high conditions of stringency according to protocols known in the art and disclosed in Maniantis et al., "Molecular Cloning" Cold Spring Harbor Press (1989).

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "host cell" or "recipient cell" encompasses any cell which contains a vector and preferably supports the replication and/or expression of the vector. Host cells may be prokaryotic cells such as *E. coli*, or eukaryotic cells such as yeast, insect, amphibian, or mammalian cells. The term as used herein means any cell which may be in culture or in vivo as part of a unicellular organism, part of a multicellular organism, or a fused or engineered cell culture.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

As used herein "promoter" includes reference to a region of DNA upstream from the start of transcription and involved in recognition and binding of RNA polymerase and other proteins to initiate transcription.

The term "protein coding sequence" means a nucleotide sequence encoding a polypeptide gene which can be used to distinguish cells expressing the polypeptide gene from those not expressing the polypeptide gene. Protein coding sequences include those commonly referred to as selectable markers. Examples of protein coding sequences include those coding a cell surface antigen and those encoding enzymes. A representative list of protein coding sequences include thymidine kinase, β-galactosidase, tryptophane synthetase, neomycin phosphotransferase, histidinol dehydrogenase, luciferase, chloramphenicol acetyltransferase, dihydrofolate reductase (DHFR); hypoxanthine guanine phosphoribosyl transferase (HGPRT), CD4, CD8 and hygromycin phosphotransferase (HYGRO).

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, and a promoter.

A "recombinant host" may be any prokaryotic or eukaryotic cell that contains either a cloning vector or an expression vector. This term also includes those prokaryotic or eukaryotic cells that have been genetically engineered to contain the clone genes in the chromosome or genome of the host cell.

The terms "recombinant virus vector" refers to any recombinant ribonucleic acid molecule having a nucleotide sequence homologous or complementary with a nucleotide sequence in an RNA virus that replicates through a DNA intermediate, has a virion RNA and utilizes reverse transcriptase for propagation of virus in a host cell. Such viruses can include those that require the presence of other viruses, such as helper viruses, to be passaged. Thus, retroviral vectors or retroviruses are intended to include those containing substantial deletions or mutations in their RNA.

As used herein the term "therapeutic gene" shall be interpreted to include any nucleotide sequence, the expression of which is desired in a host cell. This can include any genetic engineering protocol for introduction of such sequence which would benefit from reduced immunogenicity to the introduced gene and includes antisense type strategies, diagnostic protocols, or gene therapy.

As used herein, "vector" includes reference to a nucleic acid used in transfection of a host cell and into which can be inserted a polynucleotide. Vectors are often replicons. Expression vectors permit transcription of a nucleic acid inserted therein.

DESCRIPTION OF THE FIGURES

The patent or application file contains at least one drawing executed in color. Copies of this patent or patent application publication with color drawing(s) will be provided by the office upon request and payment of the necessary fee.

FIG. 9 depicts analysis of cell death in transcomplementing transduced tumors.

DETAILED DESCRIPTION OF THE INVENTION

Figure 1:
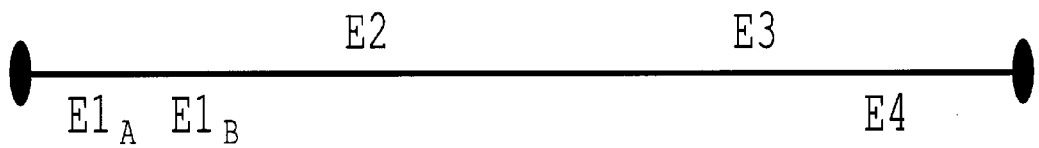
FIG. 1 is a diagram depicting the basic wild type adenovirus genome. First generation adenoviral vectors are $\Delta E1/E3^{+/-}$. These vectors all suffer from low transduction efficiency of solid tumors and typically result in less than 10% transduction.
Figure 2:
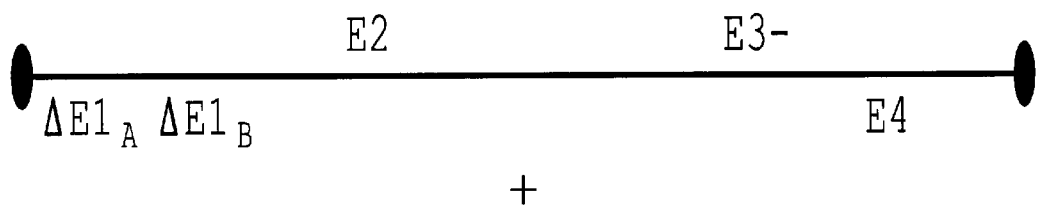
FIG. 2 depicts another adenoviral vector scheme using adenoviral vector numbers 1 and 2. This strategy (Alemany et al., 1999), uses a helper virus to supply $E1_A$ under the α-fetoprotein promoter.
Figure 2:
Figure 3:
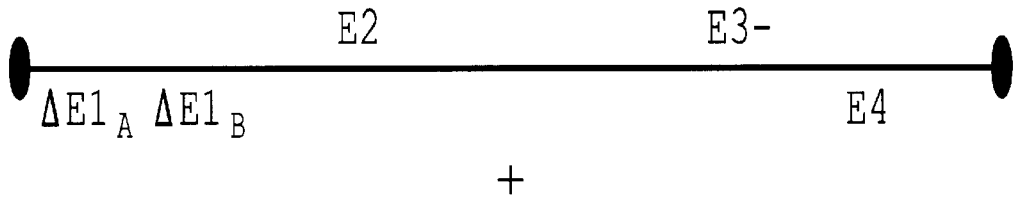
FIG. 3 is a depiction of a two-vector system of the invention.
Figure 3:
Figure 4:
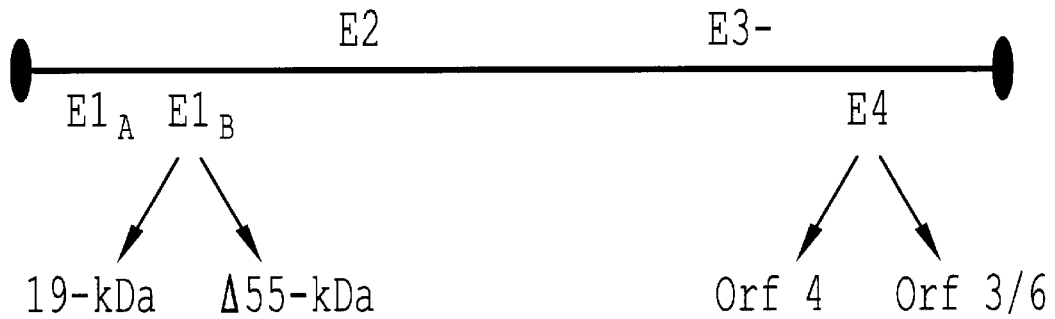
FIG. 4 depicts the strategy of improved delivery using tumor restricted replication. Bischoff et al. 1996 reported the use of Ad dl1520 ($\Delta E1_B$ 55-kDa) ONYX-015; Freytag et al., 1998, submitted a study attempting to improve this system by adding HSVtk CD fusion suicide gene; Wildner et al., 1999, used a single gene HSVtk to demonstrate a two fold increase in long term survival over tumor specific replication alone.

The following is a nonlimiting description of the adenovirus genome which may assist in designing the strategies and vectors of the invention. The Adenovirus genome is functionally divided into 2 major non-contiguous overlapping regions, early and late, based on the time of transcription after infection. The early regions are defined as those that are transcribed before the onset of viral DNA synthesis. The switch from early to late gene expression takes place about 7 hours after infection. The terms early and late are not to be taken too literally as some early regions are still transcribed after DNA synthesis has begun.

There are 6 distinct early regions; E1a, E1b, E2a, E2b, E3, and E4, each (except for the E2a–b region) with individual promoters, and one late region, which is under the control of the major late promoter, with 5 well characterized coding units (L1–L5). There are also other minor intermediate and/or late transcriptional regions that are less well characterized, including the region encoding the viral-associated (VA) RNAs. Each early and late region appears to contain a cassette of genes coding for polypeptides with related functions. Each region is transcribed initially as a single RNA which is then spliced into the mature mRNAs. More than 30 different mature RNA transcripts have been identified in Ad2, one of the most studied serotypes.

Once the viral DNA is inside the nucleus, transcription is initiated from the viral E1a promoter. This is the only viral region that must be transcribed without the aid of viral encoded trans-activators. There are other regions that are also transcribed immediately after cell infection but to a lesser extent, suggesting that the E1 region is not the only region capable of being transcribed without viral-encoded transcription factors. The E1a region codes for more than six polypeptides. One of the polypeptides from this region, a 51 kd protein, transactivates transcription of the other early regions and amplifies viral gene expression. The E1b region codes for three polypeptides. The large E1b protein (55 kd), in association with the E4 34 kd protein, forms a nuclear complex and quickly halts cellular protein synthesis during lytic infections. This 55 kd polypeptide also interacts with p53 and directly inhibits its function. A 19 kd transactivating protein encoded by the E1B region is essential to transform primary cultures. The oncogenicity of Ads in new-born rodents requires the E1 region. Similarly, when the E1 region is transfected into primary cell cultures, cell transformation occurs. Only the E1a region gene product is needed to immortalize cell cultures.

The E2a and E2b regions code for proteins directly involved in replication, i.e., the viral DNA polymerase, the pre-terminal protein and DNA binding proteins. In the E3 region, the 9 predicted proteins are not required for Ad replication in cultured cells. Of the 6 identified proteins, 4 partially characterized ones are involved in counteracting the immune system; a 19 kd glycoprotein, gp19 k, prevents cytolysis by cytotoxic T lymphocytes (CTL); and a 14.7 kd and a 10.4 kd/14.5 kd complex prevent, by different methods, E1a induced tumor necrosis factor cytolysis. The E4 region appears to contain a cassette of genes whose products act to shutdown endogenous host gene expression and upregulate transcription from the E2 and late regions. Once viral DNA synthesis begins, the late genes, coding mainly for proteins involved in the structure and assembly of the virus particle, are expressed.

The invention comprises the use of transcomplementary replication incompetent vectors, preferably adenoviral vectors. The two variants are replication deficient individually (in cis) but replication competent when combined in cells via transcomplementation. The system of the invention results in increased vector spread when introduced to tumor or other recipient cells. Any viral vector can be used according to the invention so long as two or more replication incompetent vectors are provided which, in trans are replication competent. One or both of the vectors are engineered to contain a nucleotide sequence the expression of which is desired in a host cell. The nucleotide sequence can be any sequence such as for example a therapeutic gene might be a tumor suppressor gene or a suicide gene. In one embodiment an adenoviral E4 deleted vector and an E1A/B deleted vector are introduced to recipient cells.

The compositions and methods of increasing gene transfer efficiency of viral vectors of the invention can be engineered by any of a number of techniques known to those of skill in the art of can be purchased, as many replication incompetent adenoviral vectors are commercially available and may be engineered to contain the exogenous nucleotide sequence of choice. It is to be understood that based upon the teachings herein, other viral vectors may be used in the transcomplementation scheme of the invention and are intended to be within the scope of the invention. The following is a summary of techniques for construction and transformation of the compositions and methods of the invention.

Genetic Engineering Techniques for Construction and Delivery of Vectors

A therapeutic gene to be expressed can then be introduced into the vector of the invention. The foreign DNA can comprise an entire transcription unit or expression cassette, promoter-gene-poly A or the vector can be engineered to contain promoter/transcription termination sequences such that only the gene of interest need be inserted. These types of control sequences are known in the art and include promoters for transcription initiation, optionally with an operator along with ribosome binding site sequences. Examples of such systems include beta-lactase (penicillinase) and lactose promoter systems, (Chang et al., *Nature,* 1977, 198:1056); the Tryptophan (trp) promoter system (Goeddel, et al., *Nucleic Acid Res.,* 1980, 8:4057) and the lambda derived Pl promoter and N-gene ribosome binding site (Shimatake et al., *Nature* 1981, 292:128). Other promoters such as cytomegalovirus promoter or Rous Sarcoma Virus can be used in combination with various ribosome elements such as SV40 poly A. The promoter can be any promoter known in the art including constitutive, (supra) inducible, (tetracycline-controlled transactivator (tTA)-responsive promoter (tet system, Paulus, W. et al., "Self-Contained, Tetracycline-Regulated Retroviral Vector System for Gene Delivery to Mammalian Cells", *J of Virology*, January 1996, Vol. 70, No. 1, pp. 62–67)),or tissue specific, (such as those cited in Costa, et. Al., European journal of Biochemistry, 258 "Transcriptional Regulation Of The Tissue-Type Plasminogen Activator Gene In Human Endothelial Cells: Identification Of Nuclear Factors That Recognize Functional Elements In The Tissue-Type Plasminogen Activator Gene Promoter" pgs, 123–131 (1998); Fleischmann, M., et. al., FEBS Letters 440 "Cardiac Specific Expression Of The Green Fluorescent Protein During Early Murine Embryonic Development" pgs. 370–376, (1998); Fassati, Ariberto, et. Al., Human Gene Therapy, (9:2459–2468) "Insertion Of Two Independent Enhancers In The Long Terminal Repeat Of A Self Inactivating Vector Results In High-Titer Retroviral Vectors With Tissue Specific Expression" (1998); Valerie, Jerome, et. Al. Human Gene Therapy 9:2653–2659, "Tissue Specific Cell Cycle Regulated Chimeric Transcription Factors For The Targeting Of Gene Expression To Tumor Cells, (1998); Takehito, Igarashi, et. Al., Human Gene Therapy 9:2691–2698, "A Novel Strategy Of Cell Targeting Based On Tissue-Specific Expression Of The Ecotropic Retrovirus Receptor Gene", 1998; Lidberg, Ulf et.al. The Journal of Biological Chemistry 273, No.47, "Transcriptional Regulation Of The Human Carboxyl Ester Lipase Gene In Exocrine Pancreas" 1998; Yu, Geng-Sheng et. Al., The Journal of Biological Chemistry 273 No. 49, "Co-Regulation Of Tissue-Specific Alternative Human Carnitine Palmitoyltransferase IB Gene Promoters By Fatty Acid Enzyme Substrate" (1998)). These types of sequences are well known in the art and are commercially available through several sources, ATCC, Pharmacia, Invitrogen, Stratagene, Promega.

In a preferred embodiment the expression vehicles or vectors of the invention comprising the expression system also comprise a selectable marker gene to select for transformants as well as a method for selecting those transformants for propagation of the construct in bacteria. Such selectable marker may contain an antibiotic resistance gene, such as those that confer resistance to ampicillin, kanamycin, tetracycline, or streptomycin and the like. These can include genes from prokaryotic or eukaryotic cells such as dihydrofolate reductase or multi-drug resistance I gene, hygromycin B resistance that provide for positive selection. Any type of positive selector marker can be used such as neomycin or Zeosyn and these types of selectors are generally known in the art. Several procedures for insertion and deletion of genes are known to those of skill in the art and are disclosed. For example in Maniantis, "Molecular Cloning", Cold Spring Harbor Press. See also Post et al., *Cell*, Vol. 24:555–565 (1981). An entire expression system must be provided for the selectable marker genes and the genes must be flanked on one end or the other with promoter regulatory region and on the other with transcription termination signal (polyadenylation cite). Any known promoter/transcription termination combination can be used with the selectable marker genes. For example SV40 promoter and SV40 poly A.

In a most preferred embodiment the vector comprises a specifically engineered multi-cloning site within which several unique restriction sites are created. Restriction enzymes and their cleavage sites are well known to those of skill in the art.

Any of a number of standard gene delivery transformation methods can be used with the viral vectors created according to the invention including lipid mediated transfection, receptor mediated transfection, calcium phosphate transfection, electroporation particle bombardment, naked-direct DNA injection, diethylaminoethyl (DEAE-dextran transfection).

In a preferred embodiment, the viral vector is a retroviral vector. Examples of retroviral vectors which may be employed include, but are not limited to, Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus.

The vectors of the invention are useful as agents to mediate viral-mediated gene transfer into eukaryotic cells. The replication incompetent vectors are constructed such that the majority of sequences coding for the structural genes of the virus are deleted and replaced by the therapeutic gene(s) of interest. Most often, the structural genes are removed using genetic engineering techniques known in the art. This may include digestion with the appropriate restriction endonuclease or, in some instances, with Bal 31 exonuclease to generate fragments containing appropriate portions of the vector.

Then new genes may be incorporated into the proviral backbone in several general ways. The most straightforward constructions are ones in which the structural genes of the retrovirus are replaced by a single gene which then is transcribed under the control of the viral regulatory sequences. Vectors have also been constructed which can introduce more than one gene into target cells. Usually, in such vectors one gene is under the regulatory control of the viral LTR, while the second gene is expressed either off a spliced message or is under the regulation of its own, internal promoter.

In yet another embodiment the vector comprises a Herpes Simplex Virus plasmid vector. Herpes simplex virus type-1 (HSV-1) has been demonstrated as a potential useful gene delivery vector system for gene therapy, Glorioso, J. C., "Development of Herpes Simplex Virus Vectors for Gene Transfer to the Central Nervous System. Gene Therapeutics: Methods and Applications of Direct Gene Transfer", Jon A. Wolff, Editor, 1994 Birkhauser Boston, 281–302; Kennedy, P. G., "The Use of Herpes Simplex Virus Vectors for Gene Therapy in Neurological Diseases", Q J Med, November 1993, 86(11):697–702; Latchman, D. S., "Herpes Simplex Virus Vectors for Gene Therapy", *Mol Biotechnol*, October 1994, 2(2):179–95.

HSV-1 vectors have been used for transfer of genes to muscle. Huard, J., "Herpes Simplex Virus Type 1 Vector Mediated Gene Transfer to Muscle", *Gene Therapy*, 1995, 2, 385–392; and brain, Kaplitt, M. G., "Preproenkephalin Promoter Yields Region-Specific and Long-Term Expression in Adult Brain After Direct In Vivo Gene Transfer Via a Defective Herpes Simplex Viral Vector", *Proc Natl Acad Sci USA*, Sep. 13, 1994, 91(19):8979–83, and have been used for murine brain tumor treatment, Boviatsis, E. J., "Long-Term Survival of Rats Harboring Brain Neoplasms Treated With Ganciclovir and a Herpes Simplex Virus Vector That Retains an Intact Thymidine Kinase Gene", *Cancer Res*, Nov. 15, 1994, 54(22):5745–51; Mineta, T., "Treatment of Malignant Gliomas Using Ganciclovir-Hypersensitive, Ribonucleotide Reductase-Deficient Herpes Simplex Viral Mutant", *Cancer Res*, Aug. 1, 1994, 54(15):3963–6.

Replication incompetent mini-viral vectors have been developed for easier operation and their capacity for larger insertion (up to 140 kb), Geller, Al, "An Efficient Deletion Mutant Packaging System for Defective Herpes Simplex Virus Vectors: Potential Applications to Human Gene Therapy and Neuronal Physiology", *Proc Natl Acad Sci USA*, November 1990, 87(22):8950–4; Frenkel, N., "The Herpes Simplex Virus Amplicon: A Versatile Defective Virus Vector", *Gene Therapy*. 1. Supplement 1, 1994. Replication incompetent HSV amplicons have been constructed in the art, one example is the pHSVlac vector by Geller et al, *Science,* 241, September 1988, incorporated herein by reference. These HSV amplicons contain large deletions of the HSV genome to provide space for insertion of exogenous DNA. Typically they comprise the HSV-1 packaging site, the HSV-1 "ori S" replication site and the IE 4/5 promoter sequence.

The expression system delivery composition of the present invention can be used for any diagnostic or therapeutic genetic engineering protocol including in vitro, ex vivo, or in vivo expression of a desired nucleotide sequence. For example the expression vehicles of the invention can be used in any of a number of therapeutic treatment protocols in the treatment of cancer such as by the Herpes simplex virus, thymidine kinase gene transfer system Martuza RL et al., "Experimental therapy of human glioma by means of a genetically engineered virus mutant", *Science,* 1991; 252:854–856). Also in ex vivo gene therapy protocols such as bone marrow purging (Seth P., et al., "Adenovirus-mediated gene transfer to human breast tumor cells: an approach for cancer gene therapy and bone marrow purging", *Cancer Res.* 56(6):1346–1351 (1996; Andersen, N. S., et al., "Failure of immunologic purging in mantle cell lymphoma assessed by polymerase chain reaction detection of minimal residual disease", Blood, 90(10):4212–4221 (1997)) thus when the transformed cells are reintroduced to the patient they will generate a decreased immune response. These may also be used for diagnostic purposes as well.

To fully exploit the benefits of the methods and compositions described herein, the use of many general gene therapy improvements are contemplated and are intended to be within the scope of this invention. In this manner, improvements as higher viral titer production, selection of therapeutic gene and promotor enhancer elements will be utilized, and are intended to be within the scope of the invention. These improvements are seen as simply characterized through routine experimentation and are intended to be within the scope of this invention.

All references cited herein are hereby expressly incorporated in their entirety by reference.

EXAMPLE 1

Low efficiencies of gene transfer with current viral vectors are recurrent problems for gene therapy. The most commonly used viral vectors are based on retroviruses but adenoviral vectors are seeing increased usage because of their higher efficiency of gene delivery in vivo. Despite their relative high efficiency compared to other vectors, a single direct injection of an adenoviral vector into solid tumor routinely results in less than 10% transduction of the tumor. We demonstrate in this study the use of two replication defective adenovirus vectors that cotranscomplement each other and thus allow viral replication, which enhanced both gene delivery and gene expression in the prostate tumor cell line DU 145. Specifically we used equal concentrations of an E1~E3~ deleted adenovirus containing a green fluorescent protein (GFP) reporter gene (Ad GFP) with an E4 deleted adenovirus Ad dl 1011. In vitro transduction of $2 \times 10^5$ cells DU 145 cells with Ad GFP at a multiplicity of infection of 3 (MOI) resulted in 38.3% GFP positive 24 hours after transduction as determined by fluorescent activated cell sorting FACS). DU 145 cells receiving both Ad GFP and Ad dl 1011 at a MOI of 3 resulted in 63.9% GFP positive and increased the mean fluorescent intensity by over 13 fold. We then chose to develop a spheroid tumor model based on DU 145 cells to assess the vector spread through tumor tissue. Confocal analysis of tumor spheroids transduced with Ad GFP demonstrated between 5–10% of the cells GFP positive with positive cells being observed almost exclusively on the surface of the spheroids. In contrast confocal analysis of spheroids transduced with cotranscomplementing adenoviruses demonstrated 70–90% transduction. Our use of tumor spheroids allowed investigation of vector distribution through solid tumor tissue in vitro. We demonstrate significant improvements in gene delivery and expression using transcomplementing adenoviral vectors.

The use of adenoviral based vectors for gene delivery has increased dramatically over the last five years. The favorable standing of adenovirus (Ad) vectors, until the recent death of a patient, has been due in part to their extremely efficient gene delivery in vivo. Ad vectors are relatively easily constructed using standard techniques, can be grown to high titers, and their wide tropism allows transduction of many different cell types independent of the target cell's position in cycle. These attributes coupled with the wealth of information known about the adenoviral replication strategy, life cycle, and minimal risks has propelled their wide spread use in cancer gene therapy. Even though adenoviral vectors are known to produce high levels of expression in various target tissues, they still do not provide optimal delivery when directly injected into solid tumor masses. In most tumor models reported, direct injection of replication deficient Ad vectors typically transduce less than 10% of the total tumor mass. This generalized poor gene delivery has driven the cancer gene therapist to utilize strategies which exhibit "bystander effects" in order to compensate. A more recent approach to address poor gene delivery has been the development of Ad vectors that replicate preferentially in cancer cells and spread the vector through the tumor (ONYX-015). This study was initiated to investigate the utility of using two different replication defective adenoviruses, one E1 deleted containing the GFP cDNA as a marker gene and the other virus harboring an E4 deletion without a transgene, that supply in trans the factor necessary for each of the viruses to replicate when co-administered to target cells. We hypothesize that when both vectors are co-administered to solid tumors that the probability of both viruses being delivered to the same cell and thus allowing wild type levels of replication would be quite high based on a limited volume of distribution. We also theorize that when both viruses escape the local tumor that the probability of both viruses entering the same cell will be significantly reduced because of a dramatic increase in volume of distribution. This method of increased gene delivery by replication is markedly different from other replication competent adenoviral systems that restrict replication to tumors via tumor specific promoters or lack of specific tumor suppressor gene functions. In a recent in vivo pilot study we demonstrated a 1.6 fold improvement of gene delivery by 72 hours after vector administration that increased to 3 fold by 120 hours.

TABLE 1

FACS Analysis of Mean Fluorescence Intensity of DU
145 Cells In Vitro 24 Hours After Transduction

| MOI | 3.3 | 10 | 33.3 | 100 | 333.3 |
|---|---|---|---|---|---|
| Ad GFP | 38.6 | 90.9 | 231.5 | 524.7 | 806.6 |
| Ad GFP + Ad dl1011 | 509.9 | 695.5 | 708.6 | 947.1 | 977.2 |

TABLE 2

FACS analysis of Percent GFP Positive DU 145 Cells
In Vivo 120 Hours After Transduction

| ANIMAL NUMBER | 1 | 2 | 3 | 4 | 5 | MEAN |
|---|---|---|---|---|---|---|
| Ad GFP + Ad Null | 3.4 | 3.8 | 2.0 | 1.0 | 2.1 | 2.5 |
| Ad GFP + Ad dl1011 | 6.1 | 10.7 | 0.7 | 3.2 | 2.1 | 4.6 |
| Ad GFP + Ad dl1010 | 0.3 | 4.1 | 0.9 | 2.8 | 9.7 | 3.6 |
| Ad GFP + Ad dl1020 | 9.6 | 13.1 | 9.8 | 5.7 | 0.5 | 7.7 |

TABLE 3

FACS Analysis of Mean Fluorescence Intensity of DU
145 Cells In Vivo 120 Hours After Transduction

| ANIMAL NUMBER | 1 | 2 | 3 | 4 | 5 | MEAN |
|---|---|---|---|---|---|---|
| Ad GFP + Ad Null | 212.6 | 146.6 | 224.5 | 209 | 273.1 | 212.8 |
| Ad GFP + Ad dl1011 | 157.4 | 327.4 | 133.8 | 148.2 | 206.6 | 194.7 |
| Ad GFP + Ad dl1010 | 236.6 | 280.2 | 126.5 | 361.6 | 605.7 | 322.1 |
| Ad GFP + Ad dl1020 | 279.6 | 194.6 | 265.1 | 143.3 | 475.9 | 271.7 |

EXAMPLE 2

Adrenocortical carcinomas are severe malignancies. The prognosis is poor as metastases in lung and liver soon develop, and 5-year survival rates range between 15 and 35% (Harrison et al., 1999). Two age peaks of higher incidence, in the $1^{st}$ and $4^{th}$ decades of life, have been reported (Mayer et al., 1997; Teinturier et al., 1999). Molecular, paracrine, immunologic and hormonal features of these tumors have been studied extensively and prognostic signs have been developed (Bornstein et al., 1999). Impaired cellular communication between tumor and effector cells of the immune system due to decreased $MHC^3$ class II expression (Marx et al., 1996) may be related to failed immune surveillance. Interestingly, soluble mediators of the immune system itself have been shown to promote adrenocortical tumors by the action of aberrantly expressed receptors (Willenberg et al., 1998). However, despite efforts to shed light upon the molecular and immunologic mechanisms leading to neoplastic degeneration in the adrenal gland, no effective treatments have been developed. Few chemotherapeutic options for patients bearing unresectable or metastasizing tumors are available. Standard therapies have severe side effects and their success is anecdotal (Hogan et al., 1978; Schteingart et al., 1993; Zidan et al., 1996).

Animal modeling of adrenocortical carcinoma with new treatment modalities could accelerate the development of therapies for this disease and may have broader application; however, no appropriate model is currently available to test possible treatment strategies. CE-mice have been reported to develop adrenocortical hyperplasia with progression to carcinoma after ovariectomy (Fekete et al., 1945). This is highly suggestive of an involvement of regulatory hormones; indeed, estradiol replacement prevented development of transplanted carcinomas in mice (el-Bolkainy et al., 1967). However, hormone-dependent adrenal carcinoma has not been described in humans with or without adrenal hyperplasia. To develop a more pertinent animal model of this disease, we generated SW-13-derived human adrenocortical carcinoma xenografts in nude mice. The SW-13-cell line was initiated from an hormonally inactive small-cell carcinoma of the human adrenal cortex (Leibovitz et al., 1973) and had previously been used to test compounds with some chemotherapeutic capacity (Danesi et al., 1992; LaRocca et al., 1990; Wu et al., 1989).

Gene transfer therapy could improve treatment of adrenocortical carcinomas. A principal limitation of gene therapy is inefficient gene delivery (Verma et al., 1997). Therefore, biologic amplification of anti-tumor effects against both transduced and non-transduced tumor cells has been sought via the recruitment of host immune effector cells (Nanni et al., 1999), production of antiangiogenic factors (Asselin-Paturel et al., 1999; Cao et al., 1998; Lin et al., 1998; Tanaka et al., 1997) or the use of suicide genes. The prototypic suicide gene, herpes simplex virus (hsv)-thymidine kinase (TK), activates a relatively non-toxic prodrug (i.e. Ganciclovir) to a cytotoxic compound (Moolten et al., 1986; Moolten et al., 1990). In addition to direct toxicity in the transduced cell, the expression of hsv-TK causes cell death in non-transduced tumor cells via a "bystander effect" which transfers activated prodrug from hsv-TK expressing cells to adjacent, metabolically coupled cells (Bi et al., 1993; Ishii-Morita et al., 1997; Mesnil et al., 1996; Touraine et al., 1998a).

Anti-tumor strategies have recently been modified by including viral replication as a mean of increasing intratumoral transgene delivery (Caplen et al., 1999) and as an induction of direct viral cytotoxicity (Bischoff et al., 1996; Wildner et al., 1999b). In animal models using adenoviruses with attenuated replication potential, an increased survival was demonstrated (Heise et al., 1997); and a further improvement was reported when partial replication competence was combined with suicide gene expression (Wildner et al., 1999b). However, adenoviral vectors expressing herpes simplex virus-thymidine kinase may damage proliferating non-cancerous tissues and can cause severe liver necrosis, including death in animal models after systemic application (Brand et al., 1997; van der Eb et al., 1998). Such toxicities may be even more prominent in systems using replication competent vectors expressing hsv-TK.

As a new therapeutic approach for adrenocortical cancer we modified the replicating vector strategy to utilize replication-dependent vector distribution within the tumor but sought to reduce systemic vector spread, potentially minimizing side effects. Transcomplementation of replication-defective adenovirus vectors has been achieved through supplementing with nucleic acids (Dion et al., 1996; Goldsmith et al., 1994; Ketner et al., 1989); however these nucleic acids are incapable of spread beyond the initial site of injection, the plasmid virus constructs are technically difficult to prepare, and the techniques have not obtained general usage. We elected to re-explore this strategy using transcomplementing adenoviral vectors, each encoding unique therapeutic and replicative functions. To achieve this, we employed two replication deficient adenoviral vectors, E4-deleted H5.dl1014 (Bridge et al., 1993) and an E1A/B-deleted vector carrying a herpes simplex virus-thymidine kinase gene cloned into a vector derived from H5.dl309 (AVC2.TK). The two separate adenoviral variants are replication-deficient individually due to their defects in essential viral genes (in cis-) but replication-competent when combined in cells via transcomplementation. This system was tested to establish whether replication results in increased vector spread within tumors following co-transduction and whether anti-tumor efficacy in adrenocortical tumor xenografts is improved by this approach. The in vivo tumor model was characterized by radiographic and histologic studies. We then used FACS analysis, immunohistochemistry, in situ end-labeling, and ultrastructural analyses to monitor gene transfer, virus particle production, apoptotic cell death and virus/transgene-mediated tumor lysis.

Materials and Methods

Cell Lines 293 cells (CRL-1573, Y1 cells (CCL-79), AtT20 cells (CCL-89) and SW-13 cells (CCL-105) (Liebovitz et al., 1973) were obtained from ATCC (Gaithersburg, Md.). WI62 cells were kindly provided by G. Ketner (Johns Hopkins U., Baltimore, Md.). Rat 9L cells were kindly provided by E. Oldfield (NINDS, Bethesda, Md.). All cell lines were grown in DMEM medium supplemented with 10% FCS, 2 mM L-glutamine, 100 U/mL penicillin and 100 µg/mL streptomycin (Life Technologies, Grand Island, N.Y.) at 37 ° C. in 10% $CO_2$.

Adenoviral Vectors

AVC2.null is identical to AVC2.TK except for the absence of the hsv-TK transgene and was generated by the technique of Graham (Graham et al., 1977). Briefly, the adenoviral shuttle plasmid pAVC2 (Lozier et al., 1997) was introduced into pJM17 (Graham et al., 1978) by Ca-phosphate co-precipitation technique in 293 cells (Graham et al., 1977). Recombinant E1-deleted AVC2.TK was generated by the technique of Okada (Okada et al., 1998). Hsv-TK function was confirmed by transduction of rat 9L cells at a multiplicity of infection (MOI) of 50 pfu/cell, exposure to ganciclovir, and measurement of $^3$HY-thymidine incorporation. AV.GL is an E1-deleted virus expressing green fluorescent protein under the control of the EF-1-α promoter (kindly provided by J. Wahlfors, University of Kuopio, Finland). The E4 mutant H5.dl1014 (kindly provided by G. Ketner, Johns Hopkins University) was grown on WI62 cells and isolated by standard technique. Viruses were plaque purified twice, amplified by standard technique and analyzed by restriction digestion of proteinase K-digested viral DNA. All viral stocks were plaque titered in triplicate by serial dilution and agar overlay on their respective transcomplementing cell lines according to standard protocols.

In vitro Transduction and FACS analyses

For in vitro transduction, SW-13 cells, AtT20- and Y1-cells were plated in 6-well plates at a density of 300,000 cells per well. Cells were transduced with MOIs of 1 to 100 PFU/cell. After 80 h cells were trypsinized, harvested by centrifugation and resuspended in ice-cold HBSS containing 5% FCS and 0.1 M EDTA (Sigma, St. Louis, Mo.). Cells were subjected to FACS analysis using a Becton Dickinson FACSort analyzer and 10,000 ungated events were collected for analysis.

Mice and Tumor Generation, Treatment Groups

Six-8 week-old female nude mice were obtained from DCT (Frederick, Md.). Mice were injected subcutaneously into the right flank with $10 \times 10^6$ cells in 200 µl HBSS (Biofluids, Gaithersburg, Md.) containing 20% Matrigel (Collaborative Biomedical Products, Waltham, Mass.). Weekly monitoring of tumor size was carried out by measurement diameters in three dimensions at right angles with calipers [volume=l×w×h]. In vivo transduction was performed when tumors grew to a mean volume of 300 mm$^3$. Treated tumors were injected with $2 \times 10^9$ PFU of adenoviral vector in a volume of 100 µL using 25 g needles. In some treatment groups GCV (Roche Bioscience, Palo Alto, Calif.) was injected intraperitoneally twice daily for 5 days at a dose of 100 mg/kg/d. Animals were injected with $1 \times 10^9$ PFU AVC2.TK plus $1 \times 10^9$ PFU H5.dl1014, groups [transc/GCV/80] (n=8) and [transc/GCV/30] (n=7) or $2 \times 10^9$ PFU AVC2.TK, group [TK/GCV] (n=9) to compare transcomplementing versus replication defective vector approaches of therapy. Ganciclovir was injected intraperitoneally after 80 h in group [trans/GCV/80] and additionally after 30 h in group [transc/GCV/30] to compare early and late blocking of viral replication. Two control groups [transcomp] (n=9) and [TK] (n=8) were transduced as groups [transc/GCV/80] and [TK/GCV] but did not receive GCV.[dl1014] (n=9) was transduced with $2 \times 10^9$ PFU H5.dl1014 alone, [GCV] (n=9) was only treated with GCV and [no treatment] (n=9) received neither treatment. Animals were euthanized when tumor size exceeded 1500 mm$^3$. All animal experiments were conducted in accordance with NIH guidelines for the care and treatment of laboratory animals.

Planar Imaging/Positron Emission Tomography

The accumulation of F-18 fluorodeoxyglucose (FDG) in the implanted adrenal tumors was imaged tomographically in several mice with Planar Imaging/Positron Emission Tomograph (PiPET), a device developed specifically for imaging small animals. FDG was administered by tail vein injection (150 microcuries/0.1 mL). At 30 minutes post-injection, the animal was fixed to a vertical rotation device between the two PiPET detectors, and rotated continuously for 30 min during acquisition of all possible coincidence lines connecting the two detectors. Two sequential data collections were performed with the first collection being used to visualize the subcostal regions of the animals followed by a second which visualized the more rostral areas of the animals. These two data sets were reconstructed with filtered backprojection (ramp filter) and, after various corrections, merged to form a continuous tomographic representation of the distribution of FDG in the whole animal.

Electron Microscopy

Small tissue pieces of adrenal tumor were fixed in 4% paraformaldehyde-1% glutaraldehyde in 0.1 mol/L phosphate buffer, pH 7.3, for 3 h, postfixed in 2% OsO4 in 0.1 mol/L cacodylate, pH 7.3, dehydrated in ethanol, and embedded in epoxy resin. 70 nm sections were stained with uranyl acetate and lead citrate and examined at 80 kV under a Phillips electron microscope 301 (Phillips, Rahway, N.J.).

In situ Labeling of DNA Fragments

The staining of apoptotic nuclei was achieved by non-radioactive in situ end-labeling. The free 3'-ends of cellular DNA served as template and were elongated and labeled with digoxigenin-marked deoxyUTP. The digoxigenin was subsequently immunodetected with anti-DIG-peroxidase, visualized with 3-amino-I-ethylcarbazole (AEC) and counterstained with methylene green. In additional experiments immunodetection and visualization were carried out with anti-digoxigenin-rhodamine-conjugate according to the suppliers protocol (ApopTag®-Kit, Intergen Company, Purchase, N.Y.).

Statistical Analyses

All in vitro experiments were performed in quadruplicate. Statistical analyses were performed with Prism2/GraphPad software using the Mann-Whitney test for evaluation of tumor volume experiments and the Kaplan-Meier method for survival curves. Results have been considered statistically significant if P<0.05.

Results

Figure 5:
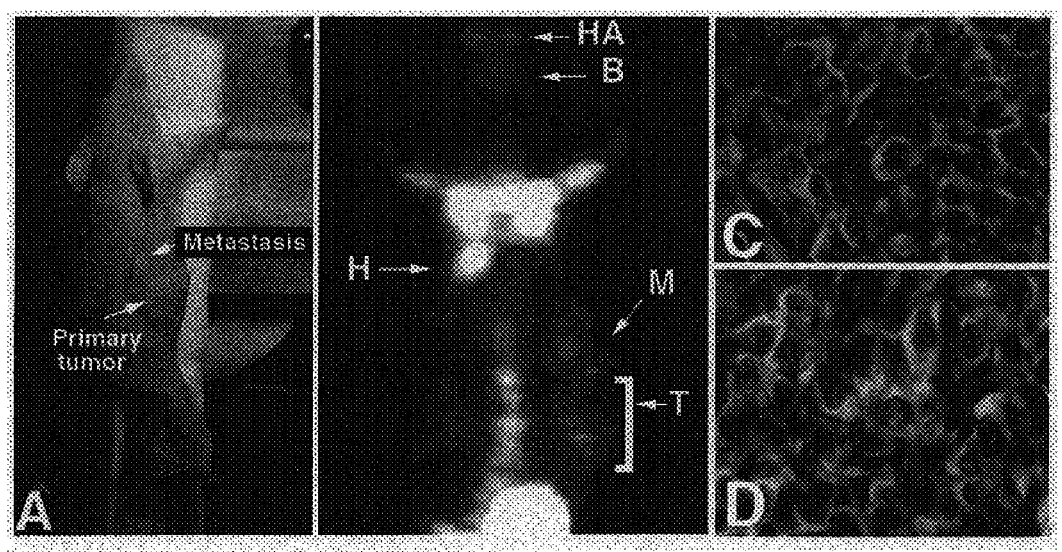
FIG. 5 depicts the human adrenocortical xenograft tumors in nude mice. (A) Female nude mice were injected subcutaneously into the right flank with $10 \times 10^6$ SW-13 cells. Prominent tumor nodules formed intra- and/or subcutaneously and after 6–7 weeks metastases occurred. (B) Whole-body volume reprojection image of an adrenal tumor-bearing mouse after injection of 18F-FDG. Primary tumor (T) and metastasis (M) are visible. Two data collections were required to visualize the whole animal (H=heart, B=brain, HA-Harderian glands) (C and D) Haematoxylin/Eosin staining of primary tumor (PRIM) and metastasis (META) from FIG. 5B. Histological studies revealed multilobulated primary tumors with an adrenal like texture. Primary tumors had a pseudo-capsule (PC) and were highly vascularized (V, vessel) and abundantly exhibited mitotic nuclei (arrowheads). Tumor cells within penetrating vessels (arrows) underline the metastatic capacity of the tumor. The histological characteristics of the tumor were identical in the metastases (40 x).

Characterization of tumor model. SW-13 derived tumor nodules were established in the flanks of nude mice by subcutaneous and/or intradermal injection of $10 \times 10^6$ cells. The adrenocortical tumor model used in this study was a progressive and lethal disease with no evidence of spontaneous regression. Animals with ulcerating tumors or tumors greater than 15% body weight were euthanized and are referred to as "succumbed to tumor burden" in the assessment of the survival rate. Tumors reached an average volume of 300 mm³ by 5 weeks after inoculation. By 8 to 10 weeks, tumor burden required euthanasia and metastases frequently could be detected by visual examination (FIG. 5A) or gross dissection. Metastatic tumor deposits were identified at multiple sites including lymph nodes or distant subcutaneous foci that could be readily localized by PET scan with $F^{18}$-FDG (FIG. 5B). Histological studies of primary and secondary tumors revealed multilobulated tumors with an adrenal glandular texture. They typically developed a pseudo-capsule and were highly vascularized. Histology of the primary and metastatic tumor deposits demonstrated characteristic signs of their common origin; both demonstrated compact cells with pleiomorphic nuclei and an abundance of mitotic figures (FIGS. 5C and D). Tumor cell masses could frequently be found on the outer side of the pseudo-capsule and occasionally within penetrating vessels. On the ultrastructural level tumors exhibited mitochondria with tubulo-vesicular structure and ample smooth endoplasmic reticulum typical of adrenocortical cells. The tumor cells did not express gap junctions by ultrastructural analysis (see FIGS. 7B and 10) or connexin 43 by immunohistochemistry (data not shown).

In vitro Transduction with AV.GL.

Figure 6:
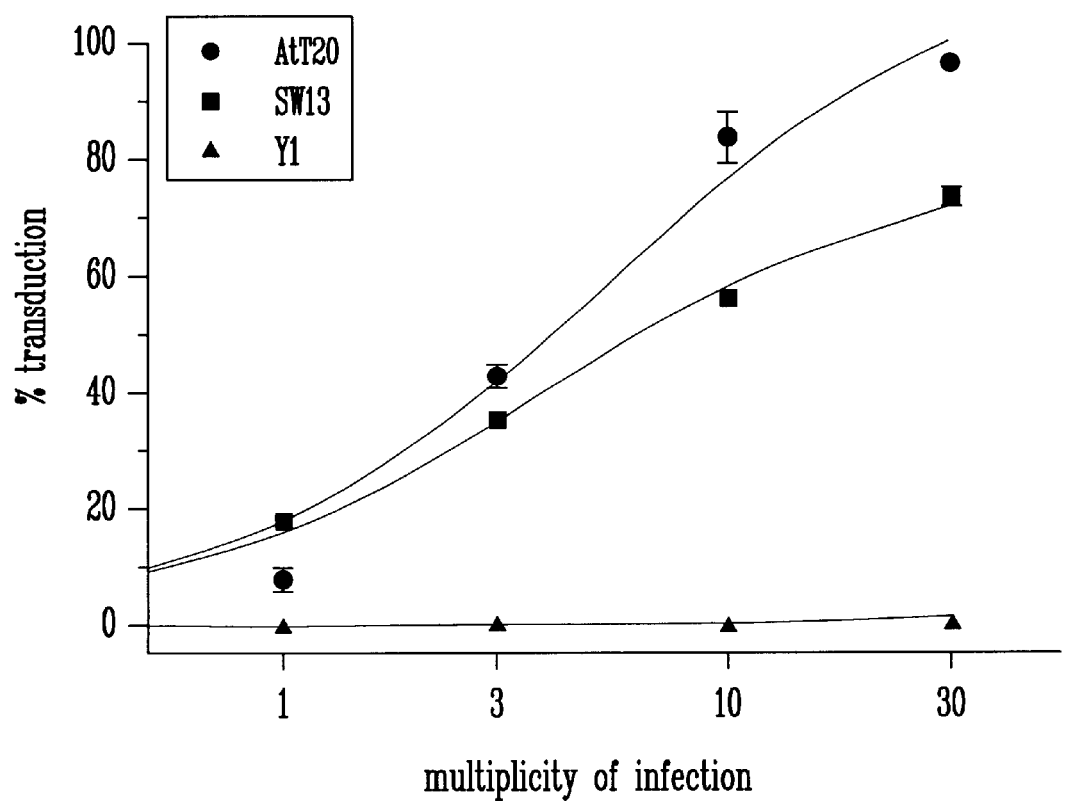
FIG. 6 depicts transduction of tumor cells in vitro. Cells plated in 6-well plates at a density of $3 \times 10^5$ cells per well were transduced with Av.GL at MOI of 1 to 100 PFU/cell, harvested after 80 h and subjected to FACS analysis. Maximum transduction for human adrenocortical SW-13 and mouse pituitary AtT20-cells was achieved at MOIs of 30PFU/cell. At higher MOIs no further increase in transduction rate could be detected and virus dependent cytotoxicity increased (data not shown).

SW-13 cells were transduced in vitro with AV.GL at MOIs of 1 to 30 PFU/cell. Transduction efficiency was compared to mouse adrenocortical Y1-cells and the pituitary cell line AtT20. A high rate of transduction in human SW-13 cells occurred at MOIs of 10 to 30 PFU/cell, whereas murine cell lines showed a vastly lower transduction rate (FIG. 6). At MOIs of 100 PFU/cell no further increase in transduction rate could be detected and virus dependent cytotoxicity increased.

In vivo Transduction and Transcomplementation.

Figure 7A:
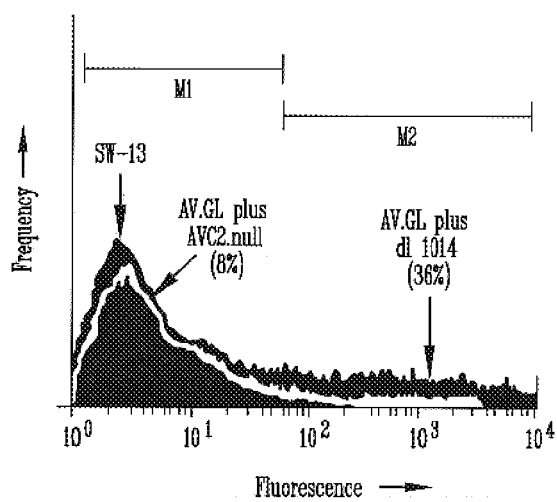
FIG. 7 depicts in vivo transduction of human adrenocortical cell xenografts. (A) Tumors were transduced in vivo with either $2 \times 10^9$ PFU AVC2.null, $1 \times 10^9$ PFU AV.GL plus $1 \times 10^9$ PFU AVC2.null or $1 \times 10^9$ PFU AV.GL plus $1 \times 10^9$ PFU H5.dl1014 and transgene expression was assessed by FACS analyses. Tumors transduced with transcomplementing vectors exhibited an up to 4 fold higher rate of transduction, median transduction efficiency was 9.8% with non-transcomplementing viruses and 36.7% for transcomplementing transduced tumors (P<0.05). (B) transmission electron micrographs demonstrating nuclear viral particles in situ. Transcomplementing transduced tumors were examined for newly assembled viral particles 96 h after transduction. De nono assembling of viral particles inside the nucleus is a characteristic feature of virus production and indicative for replication. The figure depicts characteristic adenoviral particles with circular electron dense structure and halo as nuclear inclusion in a SW-13 tumor cell.

Tumors (n=10) were transduced in vivo with either $2\times10^9$ PFU AVC2.null, $1\times10^9$ PFU AV.GL plus $1\times10^9$ PFU AVC2.null or $1\times10^9$ PFU AV.GL plus $1\times10^9$ PFU H5.dl1014. Tumors were harvested, digested with triple enzyme solution (Barth et al., 1990), and transgene expression was assessed by FACS analyses 72 and 96 h after injection. Tumors transduced with transcomplementing vectors exhibited up to 4 fold higher rates of transduction. Median transduction efficiency was 9.8% with non-transcomplementing viruses and 36.7% for tumors transduced with vectors that transcomplement (P<0.05; FIG. 7A). The percentage of transduced cells remained constant after three days suggesting that a steady state between viral de novo transduction and cell loss via viral cell lysis is reached in this time frame.

Figure 7B:
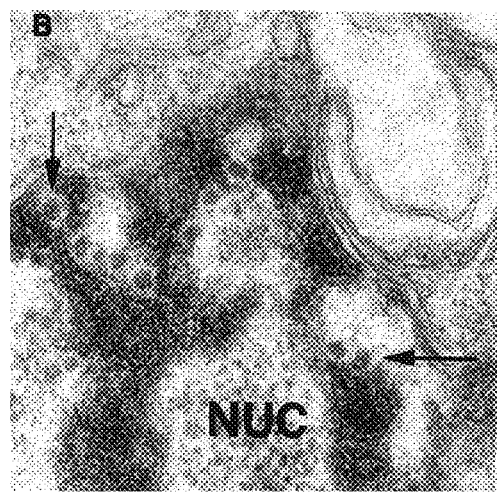

Ultrastructural analyses of the tissues was performed to detect viral particles within tumor cells as a result of viral assembly in situ. Intranuclear viral particles were detectable only when replication occurred. FIG. 7B depicts intact intranuclear viral particles in cells isolated from tumor transduced with AV.GL plus H5.dl1014. We failed to observe similar assembled particles in tumors transduced with non-transcomplementing vectors (AV.GL plus AV.null).

Treatment of Adrenocortical Cell Tumors.

Tumors with an average volume of 300 mm³ were injected with $2\times10^9$ PFU of adenoviral vector. The effect of the treatment was monitored by weekly measurements of tumor size and assessment of survival.

Survival was poor in the control groups with an average survival rate below 37% after 4 weeks and below 25% after 6 weeks, with a median survival time of 29 d. Median survival in individual groups was: [GCV]=22 d, [no treatment]=22 d, and [dl1014]=29 d. In contrast, mice with tumors transduced using AVC2.TK plus GCV treatment (group [TK/GCV]) had a notably prolonged survival (50 d, P=0.07). Similarly, animals transduced with transcomplementing vectors but without GCV also showed significantly increased survival (group [transcomp], 60.5 d, P=0.002). Importantly, administration of GCV to transcomplementing transduced animals further improved survival significantly relative to [TK/GCV] and [transcomp], (FIG. 8A, P<0.02), showing additive effects of transcomplementation and TK/GCV administration. There was no statistical difference between transcomplementation transduced animals when early (after 30 h) versus delayed (after 80 h) administration of GCV was tested, groups [transc/GCV/30] and [transc/GCV/80]. Survival in these groups declined very slowly (85% at the termination of the experiments), providing an estimated median survival time of 1.2 years by regression analyses as compared to 29 d for all controls.

Figure 8:
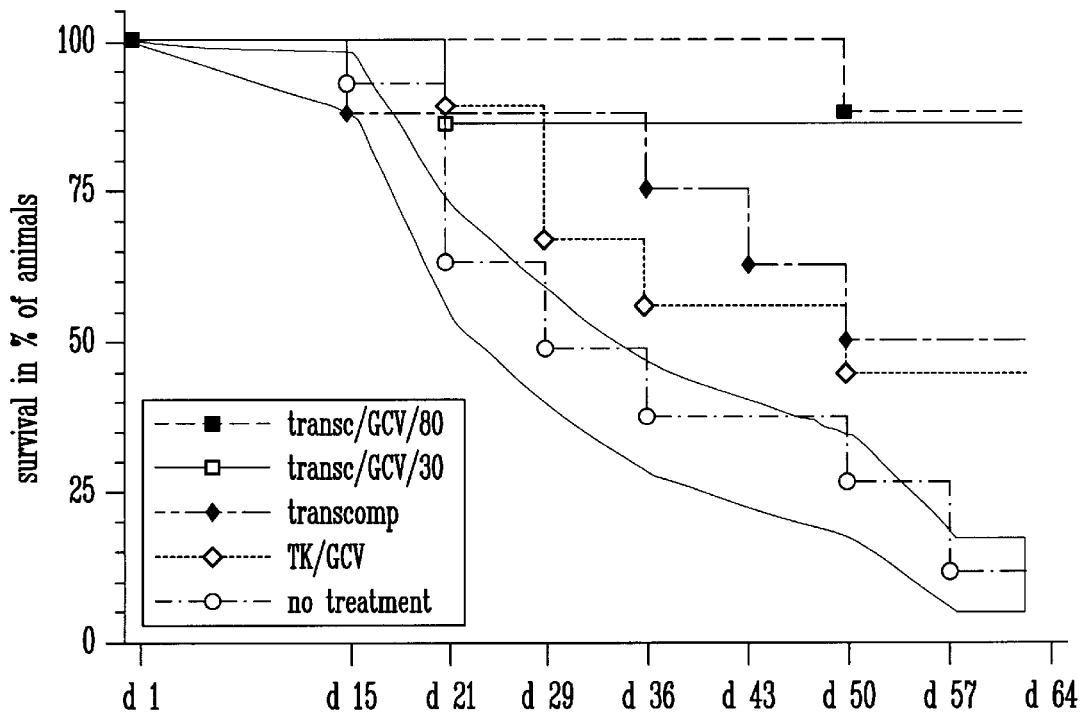
FIG. 8 depicts treatment of human adrenocortical SW-13 xenograft tumors in nude mice. Tumors with a mean volume of 300 $mm^3$ [volume=1×w×h] were transduced with $2 \times 10^9$ PFU of either transcomplementing or non-replicating adenoviral vectors. Ganciclovir (100 mg/kg/d) was given in divided doses twice daily for 5 days by intraperitoneal injection. Control animals received either viral vector without GCV or GCV alone. (A) the additive effects of TK, transcomplementation and GCV administration markedly improved survival compared to [TK/GCV] (P<0.02). Median survival time was 50 d (P=0.07) for [TK/GCV], and 60.5 d (P=0.002) for animals transduced with transcomplementing vectors but without ganciclovir [transcomp]. (B) Tumor size was monitored weekly. Growth inhibition and tumor volume reduction in animals receiving transcomplementating vectors plus GCV at 80 h [transc/GCV/80] post-transduction was superior to all other approaches, including non-replicating AVC2.TK plus GCV treatment (after 29 d; P=0.001). Transcomplementing transduction with viral replication retarded by administration of GCV at 30 h post-transduction demonstrated a noticeable, but statistically insignificant improvement comparable to AVC2.TK plus H5.dl1014 without GCV.

The improvement of survival was related to a suppression in growth of SW-13 derived tumors, which could be observed in all animals transduced with vectors expression hsv-TK and treated with GCV (groups [transc/GCV/80], [transc/GCV/30] and [TK/GCV]) within 15 days after onset of treatment. Shrinkage of the tumors in group [transc/GCV/80] continued up to 30 days after GCV treatment (FIG. 8B). Interestingly, there was a gradation of effectiveness in growth inhibition and volume shrinkage. The gradation was dependent on time allowed for completion of virus replication relative to ganciclovir administration; growth inhibition after transcomplementing transduction with GCV treatment beginning 3 h after virus administration. Both treatments were superior to transduction with AVC2.TK only plus GCV treatment (P=0.001; FIG. 8B). The tumors grew continuously in the untransduced control group [GCV] and [no treatment] and in the AVC2.TK and H5.dl1014 transduced control group [TK] and [dl1014].

Analyses of Cell Death as a Mean of Growth Retardation and Volume Reduction.

Figure 9A:
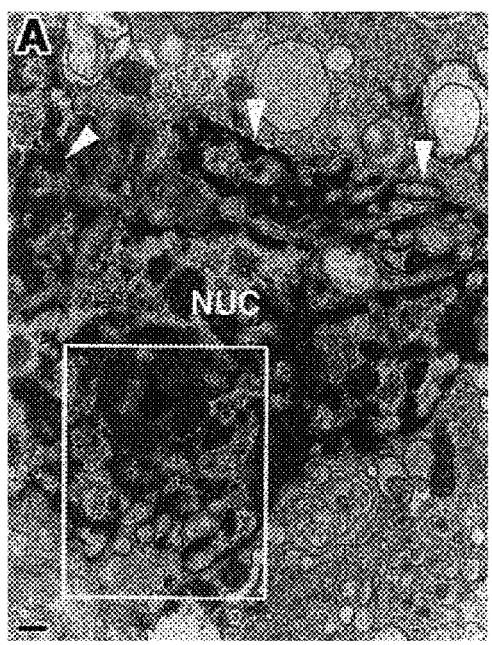
FIG. 9A depicts free 3'-ends of DNA were labeled with digoxigenin-marked deoxyUTP, subsequently immunodetected with anti-DIG-peroxidase and visualized with AEC. Red stained single nuclei and cell clusters throughout the specimen suggestive of apoptosis. Stained foci were frequently found adjacent to sites of injection and to areas demonstrating viral transduction.
Figure 9B:
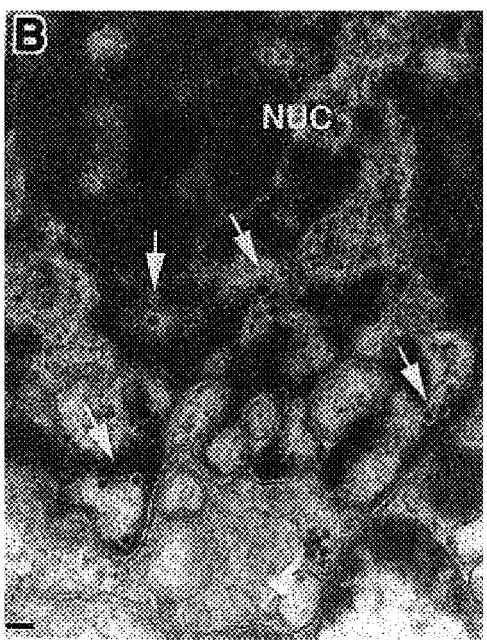
FIG. 9B shows the same section demonstrating areas viral transduction by green fluorescence of the transgene product (20×magnification).

Cell death, possibly including apoptosis, contributed to the observed growth retardation and volume reduction. To examine the prevailing cell ablating event, tumors were examined 96 hours after virus administration to explore for signs of programmed cell death induced by this therapy. The cleavage of nuclear DNA with a characteristic pattern of fragmentation is a hallmark of programmed cell death, leaving free 3'-ends of these fragments available for labeling and allows detection within a tissue specimen. In transduced SW-13 tumors we frequently observed single apoptotic nuclei as well as groups and cell clusters throughout the specimens (FIG. 9A). Clusters were frequently found adjacent to sites of injection and virus replication. Interestingly, stained nuclei suggestive of such programmed DNA cleavage or at least free 3' ends did not always completely match with the sites of viral transgene expression when GFP was used as a reporter gene (FIG. 9B).

Figure 10A:
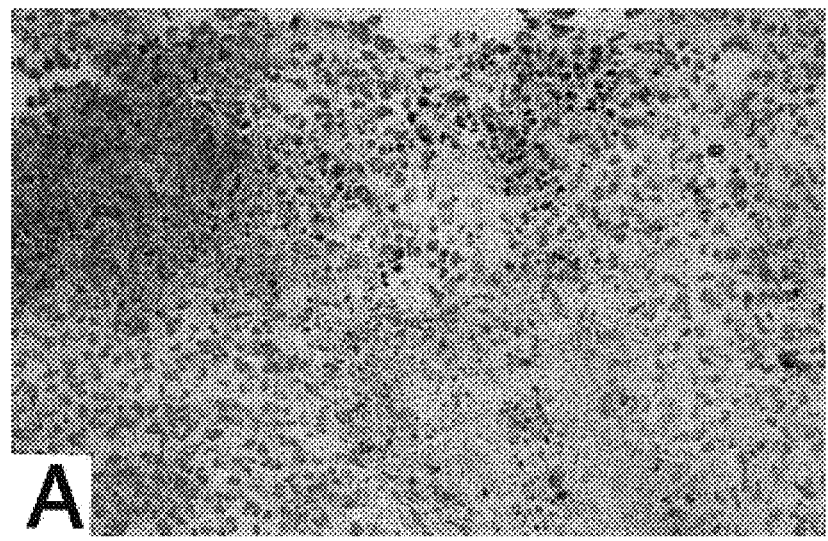
FIG. 10 depicts ultrastructural analysis of cell death in tumors Xenografts transduced with transcomplementing adenoviral vectors AVC2.TK plus H5.dl1014. Tumors exhibited mitochondria with tubulo-cristular structure typical of adrenocortical cells. (A) Cells showed apoptotic signs such as vacuolization of the nucleus (N) and cytoplasm, but only a slight condensation of chromatin and fragmentation of nuclei. The mitochondria (M) exhibited in this figure remained morphologically unaffected, indicating a grossly intact metabolism in these cells (bar=0.1 μm). (B) Higher magnification of the inset from FIG. 10A demonstrating intranuclear viral particles (arrows) indicative of viral replication.

To further examine the origins of such prominent labeling of free 3'-ends, we investigated transcomplementing transduced and non-transcomplementing-transduced tumors by electron microscopy. Ultrastructural analyses showed signs of apoptosis, as condensation of both chromatin and cytoplasm were observed as was vacuolization of the nucleus and cytoplasm. Cytosolic organelles such as mitochondria remained morphologically unaffected, indicating a grossly intact metabolism in these cells. Most often, slight condensation of chromatin and fragmentation of nuclei with blebbing and a vacuolated structure were observed, especially when the nucleus contained inclusion bodies as a sign of viral replication in the transcomplementing transduced groups (FIGS. 10A and B).

In this study, we tested virally-mediated suicide gene therapy in a human xenograft model of adrenocortical carcinoma in nude mice. Transfer of the suicide gene hsv-TK with in situ transcomplementation of vectors and the subsequent administration of the antiviral drug GCV was a powerful tool against SW-13 derived adrenocortical tumors. Transcomplementation allows viral replication and much improved distribution of transgene. The resulting anti-tumor effects of viral cytolysis and transgene-mediated tumor cell ablation yielded more effective inhibition of tumor growth and significantly increased the survival rate in this model.

Epithelial cells of human origin, such as adrenocortical SW-13 cells, are natural targets for adenovirus type 5 infection. Predictably, in vitro transduction of these cells is very efficient relative to AtT20 and Y1 cells, reflecting the natural host range of adenovirus type 5. However, adenoviruses are known as polytrope vectors and, as such, were able to transduce these other cell types, albeit at lower levels.

In this study, we used two separate viral species with either E4 (H5.dl1014) or E1A/B deletions (AVC2.TK) that are replication deficient in cis- but replication competent in co-transduced cells. Transcomplementatibn in one cell creates a permissive environment for amplification and local spread of both vectors. The selection of H5.dl1014 to transcomplement E1 defects of AVC2.TK was based on its unique properties related to the expression of E4orf4 of the E4 gene products. The E4orf4 protein itself is cytotoxic when expressed in multiple transformed cell lines (Shtrichman et al., 1998). Induction of a p53-independent pathway was implicated in the apoptotic death caused by E4orf4 expression in the cell lines that were tested (Marcellus et al., 1998). The ability of H5.dl1014 to kill transduced tumor cells beyond the focus of transcomplementation-enabled replication may greatly increase its utility as the vector that supplies the E1-transcomplementing function. Although we have not seen statistically significant anti-tumor activity of H5.dl1014 when used as a monovalent vector, no amplification and spread of the virus is possible in the absence of E4-transcomplementation and toxicity induced in 5–10% of the cells within injected tumors is undetectable by measuring tumor volumes.

Viral replication in the transcomplementing system improves transgene distribution. Cancer gene therapies are limited by poor transgene delivery within tumors (Verma et al., 1997), and increased transgene delivery/distribution of the suicide gene improves efficacy of the anti-cancer therapy. Replication-attenuated adenoviral vectors have been tested in systemic and local application strategies for biologic amplification of anti-tumor effects (Heise et al., 1999; Wildner et al., 1996b) and additive benefits after GCV treatment have been reported (Wildner et al., 1999a).

This novel transcomplementing approach yields an increasing transduction rate, dependent upon time allowed for completion of endogenous virus replication cycles. Ninety-six hours after vector injection, we find a cell transduction rate 4 fold higher than seen in transductions using non-transcomplementing vectors. In the context of the tightly packed cells of the adrenocortical carcinoma xenografts, replication and spread occurs into neighboring cells. This provides superior transgene distribution relative to replication-deficient vectors in vivo, as visualized through AV.GL-expression (FIGS. 7 and 9B). Similarly, the ability of AVC2.TK to mediate tumor cell killing in transduced cells is significantly enhanced when transcomplementation enabled amplification and spread occurs. The efficacy of the hsv-TK transgene and/or E4orf4 increases in a manner dependent upon viral replication in our system and, hereby, significantly improves estimated median survival in an additive manner when combined with GCV.

Gap junctions enable distribution (local bystander effect) or toxic GCV metabolites into neighboring cells, leading to wider cell ablation, but many human malignancies form few if any gap junctions (Trosko et al., 1998; Hyamasaki et al., 1999). In fact, the original tumor from which SW-13 was derived, was reported to not express gap junctions and in our ultrastructural and immunohistochemical analyses gap junctions could not be observed; however, gap junctions which did not contain connexin 43 could have been present, albeit infrequently. Our data is consistent with recent reports on decreased numbers of intercellular junctions in adrenocortical tumors in vivo (Murray et al, 1999). Consequently, although gap junction expression can be improved through several compounds (Touraine et al., 1998b), a greater benefit may be achieved by facilitating the spread of the suicide gene(s) in tumors lacking significant gap junctions.

Figure 10B:

The in situ end-labeling of nuclei reveals increased intratumoral apoptosis at sites both adjacent and distant to areas of viral replication following tumor transduction (FIG. 9). The prominent foci of apoptotic cell death that were observed may result from transcomplementing replication. Alternatively, it could result from transgene expression, or more likely, from direct viral cytotoxicity as apoptotic foci could be observed in tumors injected with non-replicating adenoviral vectors alone, albeit at lower frequencies. Additionally, these viruses could function as stimulants of normal apoptotic pathways that appear to be otherwise diminished in adrenocortical tumors (Wolkersdorfer et al., 1996). When GFP expression was used to localize sites of viral transduction, it became clear that exact co-localization of apoptotic nuclei with transduced cells was not always observed. This may reflect differences in the time courses of gene expression, replication, and induction of apoptotic processes as intranuclear viral particles were frequently seen in cells exhibiting signs of programmed cell death by ultrastructural analysis (FIG. 10B).

Tumor lysis by transcomplementation alone increases survival time to 60 days, consistent with recent reports on beneficial oncolytic effects through replicating adenoviral vectors without suicide genes (Alemany et al., 1999). The expression of both E1 and E4 gene products are essential for viral replication in vitro (data not shown); in vivo we find wide areas of tumor tissue subjected to cell lysis when the transcomplementing approach is used (FIG. 9). In addition, ultrastructural analyses demonstrate nuclei with many inclusion bodies and altered morphologies in treated tissues, evidence of viral replication and associated cytopathic effects.

In our nude mouse model, efficacy is dependent upon the additive effects of direct viral cytotoxicity and TK/GCV induced cell death in a fashion independent of normal immune effectors. Nevertheless, tumor lysis induced by specific gene transfer therapies is suggested to improve host immune response in some models (Nanni et al., 1999) and allows speculation of further increments in efficacy in immunocompetent organisms. Interestingly, normal adrenocortical cells express MHC class II molecules and a communication between T-lymphocytes and adrenocortical cells has been reported (Wolkersdorfer et al., 1999). The diminished MHC class II expression in adrenocortical tumors (Marx et al., 1996) may disrupt communication and, hence, be implicated in the escape of adrenocortical tumors from immune surveillance. Indeed, we have found that upregulation of MHC class I molecules occurs during apoptosis in rat glioma cells expressing hsv-TK after GCV administration and that this is associated with improved anti-tumor cytotoxic lymphocyte responses which can retard progression of, or ablate, distant tumor deposits (W.J.R., personal observation). Upregulation of MHC molecule expression induced by the therapy we describe may then improve host anti-tumor immunity in models where intact immune functions are present.

The chance of recombination-mediated reversion to wild type adenovirus is low (Sambrook et al., 1975; Williams et al., 1975) and revertants would be extremely likely to be eliminated, along with the parental viral species, when GCV is added to the co-transduced cells. This restricted opportunity for the generation and release of pseudo-wild type revertants must still be carefully considered and addressed when the transcomplementing approach should be used in a clinical setting. Inadvertent dissemination or systemic application of vectors, expressing hsv-TK, and even inactivated virus particles lacking transgene expression, may cause severe liver damage, inflammation and necrosis, and even death in rodent models (Brand et al., 1997; van der Eb et al., 1998). Similarly, liver toxicity through non-replicating vector administration has been seen in primates (Lozier et al., 1999).

Cells infected with H5.dl1014 express only the orf4 peptide of early region 4 and, therefore, exhibit downregulation of the activity of E1A proteins in the absence of E4orf6 or E4orf3. This reduces the expression of viral genes dependent upon E1A R289 phosphorylation and causes a severe viral DNA replication defect (Bondesson et al., 1996; Kleinberger et al., 1993; Muller et al., 1992).

In summary, our findings demonstrate that this novel transcomplementing system of adenoviral vectors significantly enhances hsv-TK/GCV suicide gene therapy for cancer. Blockade of tumor growth improves and survival time is greatly prolonged. The mechanisms underlying tumor growth retardation and/or ablation involve increased replication-dependent cytolysis and more efficient transgene delivery, which provide improved local bystander effects and are characterized by a high frequency of apoptotic cell death in transcomplementing transduced tumors. Transcomplementing vectors are a promising system displaying enhanced local transduction rates but low systemic toxicity. When used as vehicle for delivery of the hsv-TK transgene, significant therapeutic benefits are observed in a model of adrenocortical cancer. This approach may be refined to become a new treatment option for patients with advanced adrenal cancer or other tumors.

ALEMANY, R., LAI, S., LOU, Y. C., JAN, H. Y., FANG, X., and ZHANG, W. W. (1999). Complementary adenoviral vectors for oncolysis. Cancer Gene Ther. 6, 21–25.

ASSELIN-PATUREL, C., LASSAU, N., GUINEBRETIERE, J. M., ZHANG, J., GAY, F., BEX, F., HALLEZ, S., LECLERE, J., PERONNEAU, P., MAMI-CHOUAIB, F., and CHOUAIB, S. (1999). Transfer of the murine interleukin-12 gene in vivo by a Semliki Forest virus vector induces B16 tumor regression through inhibition of tumor blood vessel formation monitored by Doppler ultrasonography [In Process Citation]. Gene Ther. 6, 606–615.

BARTH, R. J. J., BOCK, S. N., MULÉ, J. J., and ROSENBERG, S. A. (1990). Unique murine tumor-associated antigens identified by tumor infiltrating lymphocytes. J Immunol. 144, 1531–1537.

BI, W. L., PARYSEK, L. M., WARNICK, R., and STAMBROOK, P. J. (1993). In vitro evidence that metabolic cooperation is responsible for the bystander effect observed with HSV tk retroviral gene therapy. Hum. Gene Ther. 4, 725–731.

BISCHOFF, J. R., KIRN, D. H., WILLIAMS, A., HEISE, C., HORN, S., MUNA, M., NG, L., NYE, J. A., SAMPSON-JOHANNES, A., FATTAEY, A., and MCCORMICK, F. (1996). An adenovirus mutant that replicates selectively in p53-deficient human tumor cells [see comments]. Science. 274, 373–376.

BONDESSON, M., OHMAN, K., MANERVIK, M., FAN, S., and AKUSJÄRVI, G. (1996). Adenovirus E4 open reading frame 4 protein autoregulates E4 transcription by inhibiting E1A transactivation of the E4 promoter. J. Virol. 70, 3844–3851.

BORNSTEIN, S. R., STRATAKIS, C. A., and CHROUSOS, G. P. (1999). Adrenocortical tumors: recent advances in basic concepts and clinical management. Ann. Intern. Med. 130, 759–771.

BRAND, K., ARNOLD, W., BARTELS, T., LIEBER, A., KAY, M. A., STRAUSS, M., and DORKEN, B. (1997). Liver-associated toxicity of the HSV-tk/GCV approach and adenoviral vectors. Cancer Gene Ther. 4, 9–16.

BRIDGE, E., MEDGHALCHI, S., UBOL, S., LEESONG, M., and KETNER, G. (1993). Adenovirus early region 4 and viral DNA synthesis. Virology. 193, 794–801.

CAO, Y., O'REILLY, M. S., MARSHALL, B., FLYNN, E., JI, R. W., and FOLKMAN, J. (1998). Expression of angiostatin cDNA in a murine fibrosarcoma suppresses primary tumor growth and produces long-term dormancy of metastases. J. Clin. Invest. 101, 1055–1063.

CAPLEN, N. J., HIGGINBOTHAM, J. N., SCHEEL, J. R., VAHANIAN, N., YOSHIDA, Y., HAMADA, H., BLAESE, R. M., and RAMSEY, W. J. (1999). Adeno-retroviral chimeric viruses as in vivo transducing agents. Gene Ther. 6, 454–459.

DANESI, R., AGEN, C., BERNARDINI, N., COSTA, M., and DEL TACCA, M. (1992). The antiproliferative effect of suramin on the cancer cell line SW-13 is mediated by the inhibition of transforming growth factor beta 1 (TGF-beta 1). Pharmacol. Res. 25 Suppl 1:17–8, 17–18.

DION, L. D., GOLDSMITH, K. T., and GARVER, R. I. J. (1996). Quantitative and in vivo activity of adenoviral-producing cells made by cotransduction of a replication-defective adenovirus and a replication-enabling plasmid. Cancer Gene Ther. 3, 230–237.

EL-BOLKAINY, M. N., PIERCE, G. B. J., and FRENCH, A. J. (1967). Regression of an adrenal cortical carcinoma by estradiol treatment. Cancer Res. 27, 1846–1854.

FEKETE, E. and LITTLE, C. C. (1945). Histological study of adrenal cortical carcinoma in gonadectomized mice of the ce strain. Cancer Res. 5, 220–226.

GOLDSMITH, K. T., CURIEL, D. T., ENGLER, J. A., and GARBER, R. I. J. (1994). Trans complementation of an E1A-deleted adenovirus with codelivered E1A sequences to make recombinant adenoviral producer cells. Hum Gene Ther. 5, 1341–1348.

GRAHAM, F. L., HARRISON, T., and WILLIAMS, J. (1978). Defective transforming capacity of adenovirus type 5 host-range mutants. Virology. 86, 10–21.

GRAHAM, F. L., SMILEY, J., RUSSELL, W. C., and NAIRN, R. (1977). Characteristics of a human cell line tranformed by DNA from human adenovirus type 5. J. Gen. Virol. 36, 59–74.

HARRISON, L. E., GAUDIN, P. B. and BRENNAN, M. F. (1999). Pathologic features of prognostic significance for adrenocortical carcinoma after curative resection. Arch. Surg. 134, 181–185.

HEISE, C., SAMPSON-JOHANNES, A., WILLIAMS, A., MCCORMICK, F., VON HOFF, D. D., and KIRN, D. H. (1997). ONYX-015, an E1B gene-attenuated adenovirus, causes tumor-specific cytolysis and antitumoral efficacy that can be augmented by standard chemotherapeutic agents [see comments]. Nat. Med. 3, 639–645.

HEISE, C. C., WILLIAMS, A. M., XUE, S., PROPST, M., and KIRN, D. H. (1999). Intravenous administration of ONYX-015, a selectively replicating adenovirus, induces antitumoral efficacy. Cancer Res. 59, 2623–2628.

HOGAN, T. F., CITRIN, D. L., JOHNSON, B. M., NAKAMURA, S., DAVIS, T. E., and BORDEN, E. C. (1978). o,p'-DDD (mitotane) therapy of adrenal cortical carcinoma: observations on drug dosage, toxicity, and steroid replacement. Cancer. 42, 2177–2181.

ISHII-MORITA, H., AGBARIA, R., MULLEN, C. A., HIRANO, H., KOEPLIN, D. A., RAM, Z., OLDFIELD, E. H., JOHNS, D. G., and BLAESE, R. M. (1997). Mechanism of 'bystander effect' killing in the herpes simplex thymidine kinase gene therapy model of cancer treatment. Gene Ther. 4, 244–251.

KETNER, G., BRIDGE, E., VIRTANEN, A., HEMSTROM, C., and PETTERSON, U. (1989). Complementation of adenovirus E4 mutants by transient expression of E4 cDNA and deletion plasmids. Nucleic Acids Res. 17, 3037–3048.

KLEINBERGER, T. and SHENK, T. (1993). Adenovirus E4orf4 protein binds to protein phosphatase 2A, and the complex down regulates E1A-enhanced junB transcription. J Virol. 67, 7556–7560.

LAROCCA, R. V., STEIN, C. A., DANESI, R., JAMIS-DOW, C. A., WEISS, G. H., and MYERS, C. E. (1990). Suramin in adrenal cancer: modulation of steroid hormone production, cytotoxicity in vitro, and clinical antitumor effect. J. Clin. Endocrinol. Metab. 71, 497–504.

LEIBOVITZ, A., MCCOMBS, W. M., JOHNSTON, D., MCCOY, C. E., and STINSON, J. C. (1973). New human cancer cell culture lines. I. SW-13, small-cell carcinoma of the adrenal cortex. J. Natl. Cancer Inst. 51, 691–697.

LIN, P., BUSTON, J. A., ACHESON, A., RADZIEJEWSKI, C., MAISONPIERRE, P. C., YANCOPOULOS, G. D., CHANNON, K. M., HALE, L. P., DEWHIRST, M. W., GEORGE, S. E., and PETERS, K. G. (1998). Antiangiogenic gene therapy targeting the endothelium-specific receptor tyrosine kinase Tie2. Proc. Natl. Acad. Sci. U.S.A. 95, 8829–8834.

LOZIER, J. N., METZGER, M. E., DONAHUE, R. E., and MORGAN, R. A. (1999). The rhesus macaque as an animal model for hemophilia B gene therapy. Blood. 93, 1875–1881.

LOZIER, J. N., YANKASKAS, J. R., RAMSEY, W. J., CHEN, L., BERSCHNEIDER, H., and MORGAN, R. A. (1997). Gut epithelial cells as targets for gene therapy of hemophilia. Hum. Gene Ther. 8, 1481–1490.

MARCELLUS, R. C., LAVOIE, J. N., BOIVIN, D., SHORE, G. C., KETNER, G., and BRANTON, P. E. (1998). The early region 4orf4 protein of human adenovirus type 5 induces p53-independent cell death by apoptosis. J. Virol. 72, 7144–7153.

MARX, C., WOLKERSDORFER, G. W., BROWN, J. W., SCHERBAUM,. W. A., and BORNSTEIN, S. R. (1996). MHC class II expression—a new tool to assess dignity in adrenocortical tumours. J. Clin. Endocrinol. Metab. 81, 4488–4491.

MAYER, S. K., OLIGNY, L. L., DEAL, C., YAZBECK, S., GAGNE, N., and BLANCHARD, H. (1997). Childhood adrenocortical tumors: case series and reevaluation of prognosis—a 24-year experience. J. Pediatr. Surg. 32, 911–915.

MESNIL, M., PICCOLI, C., TIRABY, G., WILLECKE, K., and YAMASAKI, H. (1996). Bystander killing of cancer cells by herpes simplex virus thymidine kinase gene is mediated by connexins. Proc. Natl. Acad. Sci. U.S.A. 93, 1831–1835.

MOOLTEN, F. L. (1986). Tumor chemosensitivity conferred by inserted herpes thymidine kinase genes: paradigm for a prospective cancer control strategy. Cancer Res. 46, 5276–5281.

MOOLTEN, F. L. and WELLS, J. M. (1990). Curability of tumors bearing herpes thymidine kinase genes transferred by retroviral vectors. J. Natl. Cancer Inst. 82, 297–300.

MURRAY, S. A., FISHMAN, L. A., BROWN, J., and BORNSTEIN, S. R. Expression of gap junction protein is decreased in human adrenocortical tumors. J. Clin. Endocrinol. Metab. 1999. Ref Type: In Press MULLER, U., KLEINBERGER, T., and SHENK, T. (1992). Adenovirus E4orf4 protein reduces phosphorylation of c-Fos and E1A proteins while simultaneously reducing the level of AP-1. J. Virol. 66, 5867–5878.

NANNI, P., FORNI, G., and LOLLINI, P. L. (1999). Cytokinegene therapy: hopes and pitfalls. Ann. Oncol. 10, 261–266.

OKADA, T., RAMSEY, W. H., MUNIR, J., WILDNER, O., and BLAESE, R. M. (1998). Efficient directional cloning of recombinant adenovirus vectors using DNA-protein complex. Nucleic. Acids. Res. 26, 1947–1950.

SAMBROOK, J., WILLIAMS, J., SHARP, P. A., and GRODZICKER, T. (1975). Physical mapping of temperature-sensitive mutations of adenoviruses. J Mol. Biol. 97, 369–390.

SCHTEINGART, D. E., SINSHEIMER, J. E., COUNSELL, R. E., ABRAMS, G. D., MCCLELLAN, N., DJANEGARA, T., HINES, J., RUANGWISES, N., BENITEZ, R., and WOTRING, L. L. (1993). Comparison of the adrenalytic activity of mitotane and a methylated homolog on normal adrenal cortex and adrenal cortical carcinoma. Cancer Chemother. Pharmacol. 31, 459–466.

SHTRICHMAN, R. and KLEINBERGER, T. (1998). Adenovirus type 5 E4 open reading frame 4 protein induces apoptosis in transformed cells. J Virol. 72, 2975–2982.

TANAKA, TL, MANOME, Y., WEN, P., KUFE, D. W., and FINE, H. A. (1997). Viral vector-mediated transduction of a modified platelet factor 4 cDNA inhibits angiogenesis and tumor growth. Nat. Med. 3, 437–442.

TEINTURIER, C., PAUCHARD, M. S., BRUGIERES, L., LANDAIS, P., CHAUSSAIN, J. L., and BOUGNERES, P. F. (1999). Clinical and prognostic aspects of adrenocortical neoplasms in childhood. Med. Pediatr. Oncol. 32, 106–111.

TOURAINE, R. L., ISHII-MORITA, H., RAMSEY, W. J., and BLAESE, R. M. (1998a). The bystander effect in the HSVtk/ganciclovir system and its relationship to gap junctional communication. Gene Ther. 5, 1705–1711.

TOURAINE, R. L., VAHANIAN, N., RAMSEY, W. J., and BLAESE, R. M. (1998b). Enhancement of the herpes simplex virus thymidine kinase/ganciclovir bystander effect and its antitumor efficacy in vivo by pharmacologic manipulation of gap junctions. Hum Gene Ther. 9, 2385–2391.

TROSKO, J. E. and RUCH, R. J. (1998). Cell-cell communication in carcinogenesis [In Process Citation]. Front. Biosci. 3:D208–36, D208-D236.

VAN DER EB, M. M., CRAMER, S. J., VERGOUWE, Y., SCHAGEN, F. H., VAN KRIEKEN, J. H., VAN DER EB, A. J., RINKES, I. H., VAN DE VELDE, C. J., and HOEBEN, R. C. (1998). Severe hepatic dysfunction after adenovirus-mediated transfer of the herpes simplex virus thymidine kinase gene and ganciclovir administration. Gene Ther. 5, 451–458.

VERMA, I. M., and SOMIA, N. (1997). Gene therapy—promises, problems and prospects [news]. Nature. 389, 239–242.

WILDNER, O., BLAESE, R. M., and MORRIS, J. C. (1999a). Therapy of colon cancer with oncolytic adenovirus is enhanced by the addition of herpes simplex virus-thymidine kinase. Cancer Res. 59, 410–413.

WILDNER, O., MORRIS, J. C., VAHANIAN, N. N., FORD, H. J., RAMSEY, W. J., and BLAESE, R. M. (1999b). Adenoviral vectors capable of replication improve the efficacy of HSVtk/GCV suicide gene therapy of cancer. Gene Ther. 6, 57–62.

WILLENBERG, H. S., STRATAKIS, C. A., MARX, C., EHRHART-BORNSTEIN, M., CHROUSOS, G. P., and BORNSTEIN, S. R. (1998). Aberrant interleukin-1 receptors in a cortisol-secreting adrenal adenoma causing Cushing's syndrome. N. Engl. J. Med. 339, 27–31.

WILLIAMS, J., GRODZICKER, T., SHARP, P., and SAMBROOK, J. (1975). Adenovirus recombination: physical mapping of crossover events. Cell. 4, 113–119.

WOLKERSDORFER, G. W., LOHMANN, T., CHRISTIAN MARX, SCHRODER, S., PFEIFFER, R., STAHL, H-D, SCHERBAUM, W. A., CHROUSOS, G. P., and BORNSTEIN, S. R. Lymphocytes stimulate dehydroepiandrosterone production through direct cellular contact with adrenal zona reticularis cells: A novel mechanism of immune-endocrine interaction. ENDO '99, $81^{st}$ Annual Meeting of The Endocrine Society, 12.-15.6.99, San Diego, U.S.A. 1999. Ref Type: Abstract WOLKERSDORFER, G. W., MARX, C., BROWN, J. W., SCHERBAUM, W. A., and BORNSTEIN, S. R. (1996). Evaluation of apoptotic parameters in normal and neoplastic human adrenal. Endocr. Res. 22, 411–419.

WU, Y. W., CHIK, C. L., and KNAZEK, R. A. (1989). An in vitro and in vivo study of antitumor effects of gossypol on human SW-13 adrenocortical carcinoma. Cancer Res. 49, 3754–3758.

YAMASAKI, H., KRUTOVSKIKH, V., MESNIL, M., TANAKA, T., ZAIDAN-DAGLI, M. L., and OMORI, Y. (1999). Role of connexin (gap junction) genes in cell growth control and carcinogenesis. C.R. Acad. Sci. III. 322, 151–159.

EXAMPLE 3

The method of the invention is shown with various combinations of vectors. dl1011 is a E4 mutant with a deletion of the entire E4 region. 1014 is a mutant with open reading frame 4 expressed.

Figure 11:
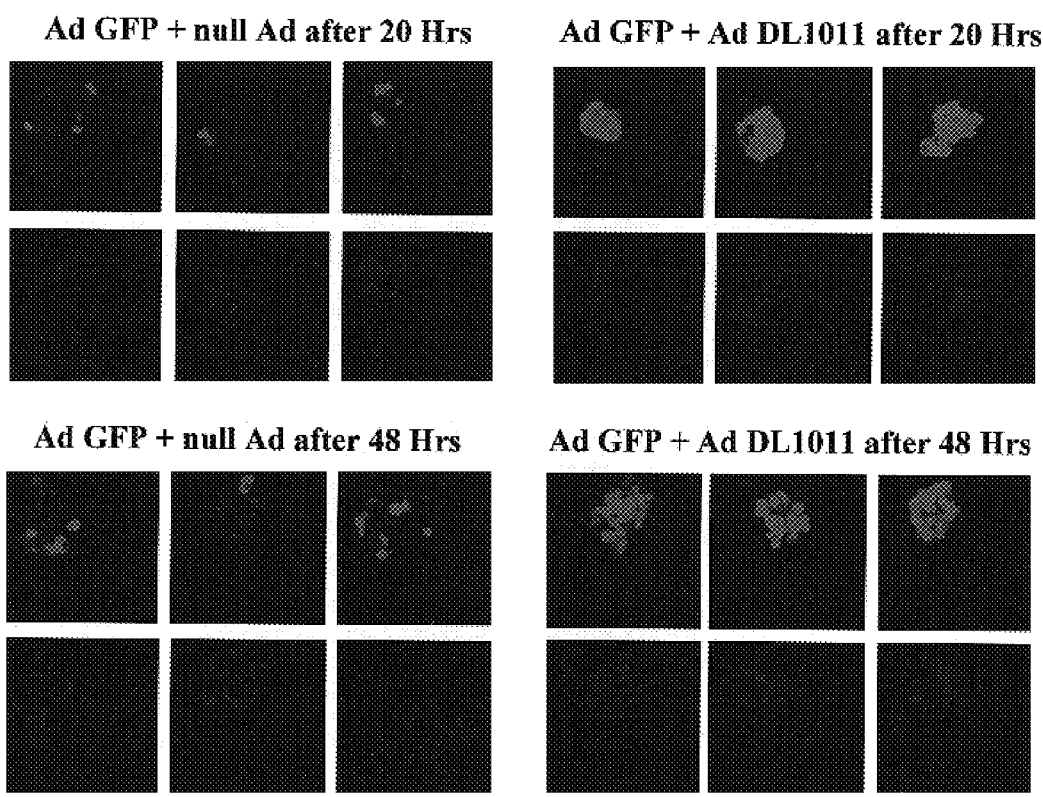
FIG. 11 depicts DU 145 spheroids were transduce with Ad GFP+Ad Null or Ad GFP+Ad dl1011 and subjected to confocal microscopy.

FIG. 11 are photographs depicting DU 145 spheroids transduce with Ad GFP+Ad Null or Ad GFP+Ad dl1011 and subjected to confocal microscopy. As can be seen the combination of AdGFP and AD DL 1011 showed marked increase in GFP expression levels over the individual vectors.

Figure 12:
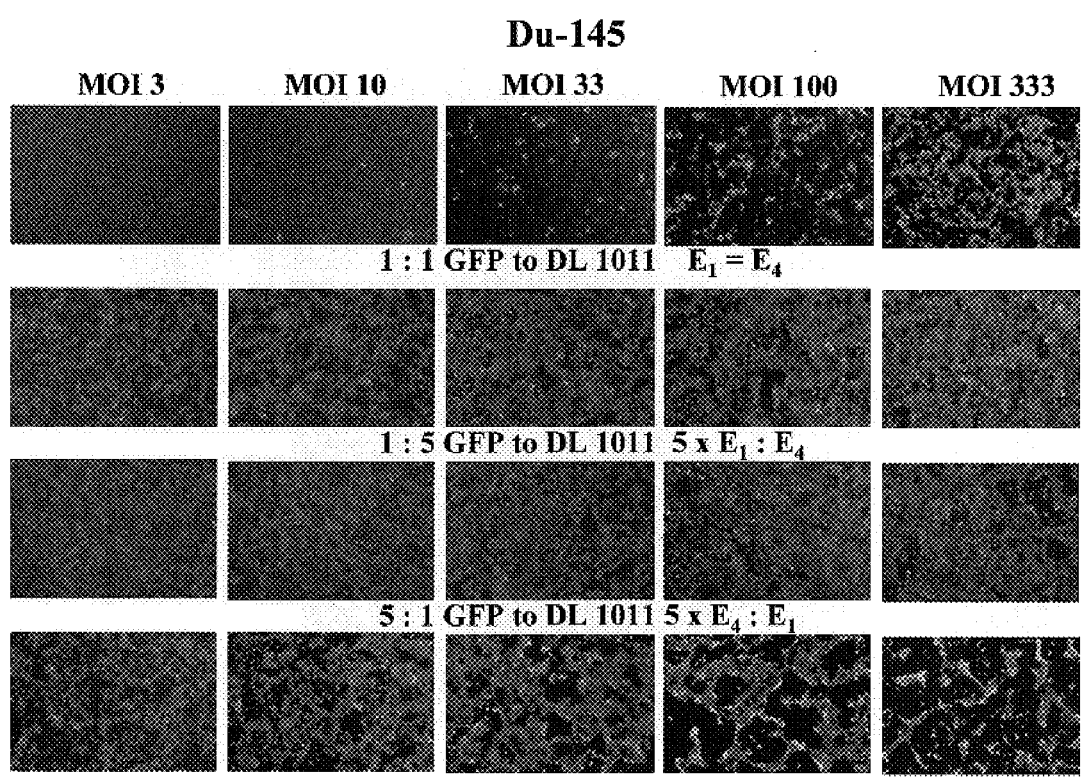
FIG. 12 depicts DU 145 Cells were transduced with various ratios of Ad GFP+Ad Null or Ad GFP+Ad dl1011 and photographed at 20 hrs.

FIG. 12 shows DU 145 cells transduced with various ratios of Ad GFP+Ad Null or Ad GFP+Ad dl1011 and photographed at 20 hrs. The combination of Ad GFP and Ad dl1011 gave similar GFP levels with up to 1 log lower vector dose.

Figure 13A:
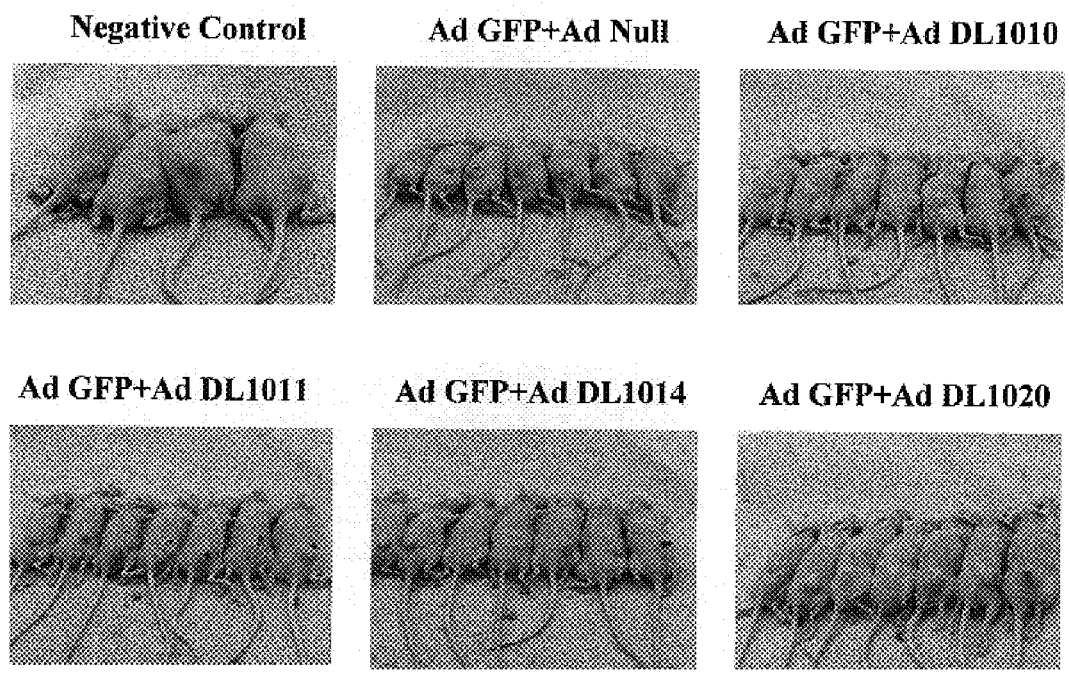
FIGS. 13(a–c) depict HCT 115 tumors were injected $1 \times 10^8$ PFU with Ad GFP+Ad Null or Ad GFP+Ad dl1011 or Ad GFP+Ad dl1010 or Ad GFP+Ad dl1014 or Ad GFP+Ad dl1020 and tumors photographed at the indicated times.
Figure 13B:
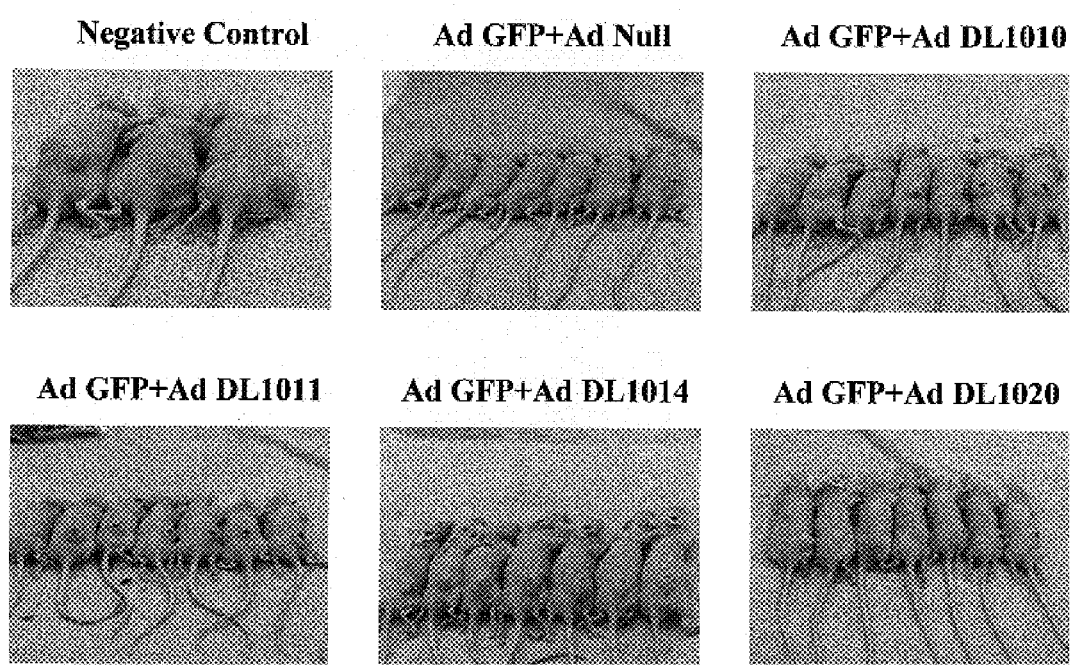
Figure 13C:
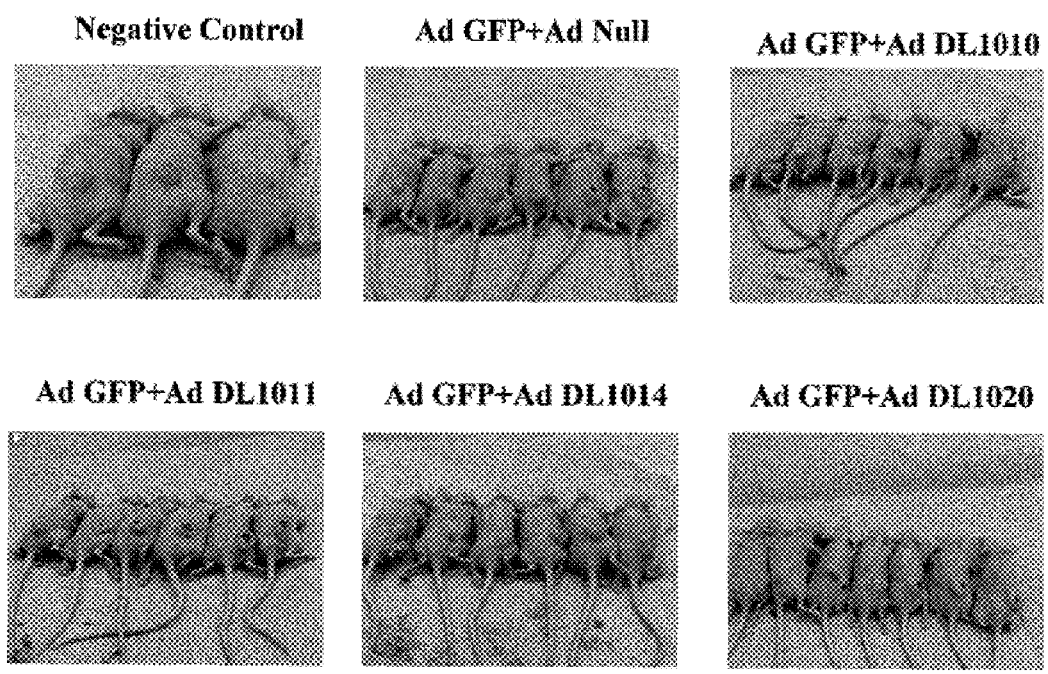

FIGS. 13a–c depict mice with HCT 115 tumors injected. $1 \times 10^8$ PFU with Ad GFP+Ad Null or Ad GFP+Ad dl1011 or Ad GFP+Ad dl1010 or Ad GFP+Ad dl1014 or Ad GFP+Ad dl1020 and tumors photographed at the indicated times. The replication competent vectors demonstrated up to 60% tumor regression.

Figure 14A:
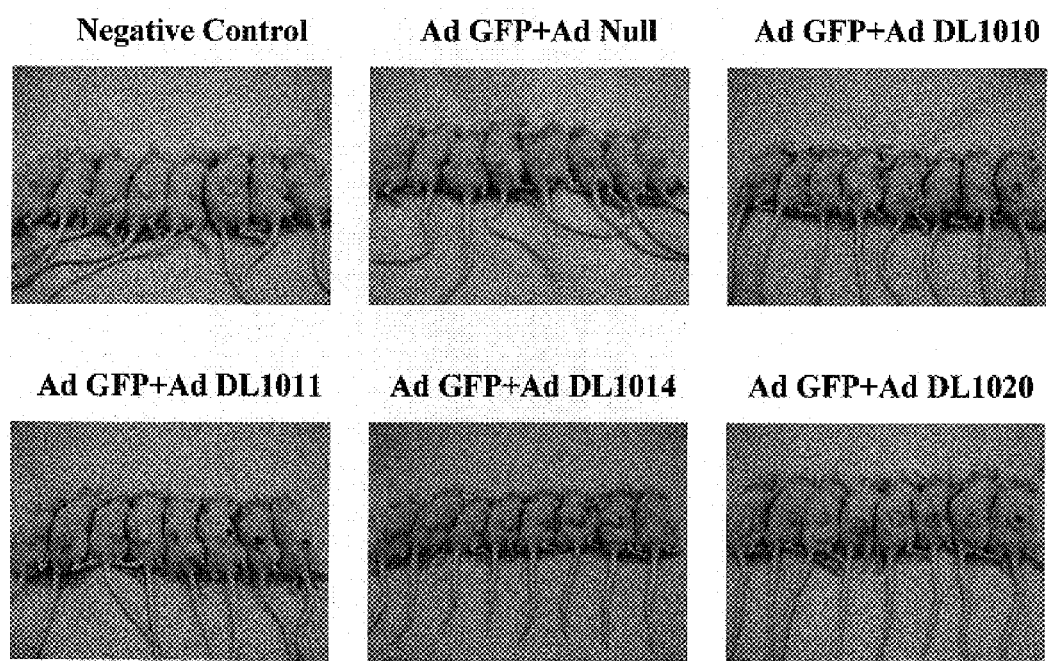
FIGS. 14(a–c) depict HTC 116 tumors were injected 1×10⁸ PFU with ADGFP+Ad Null or AdGFP+Ad dl1011 or AdGFP+Ad dl1010 or AdGFP+Ad dl1014 or Ad GFP+Ad dl1020 and tumors photographed at the indicated times.
Figure 14B:
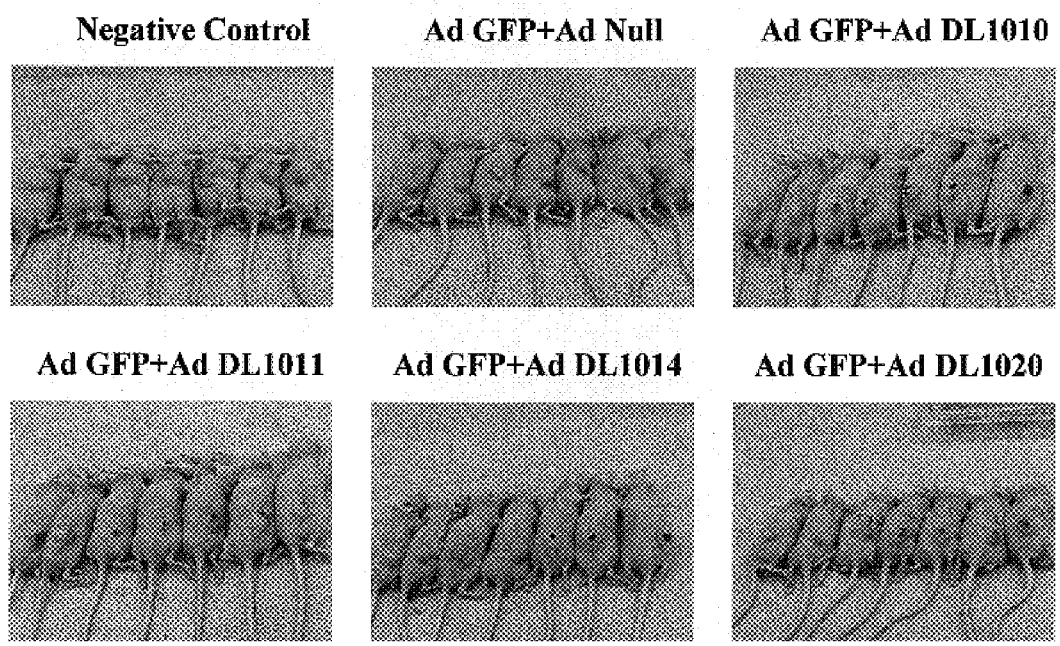
Figure 14C:
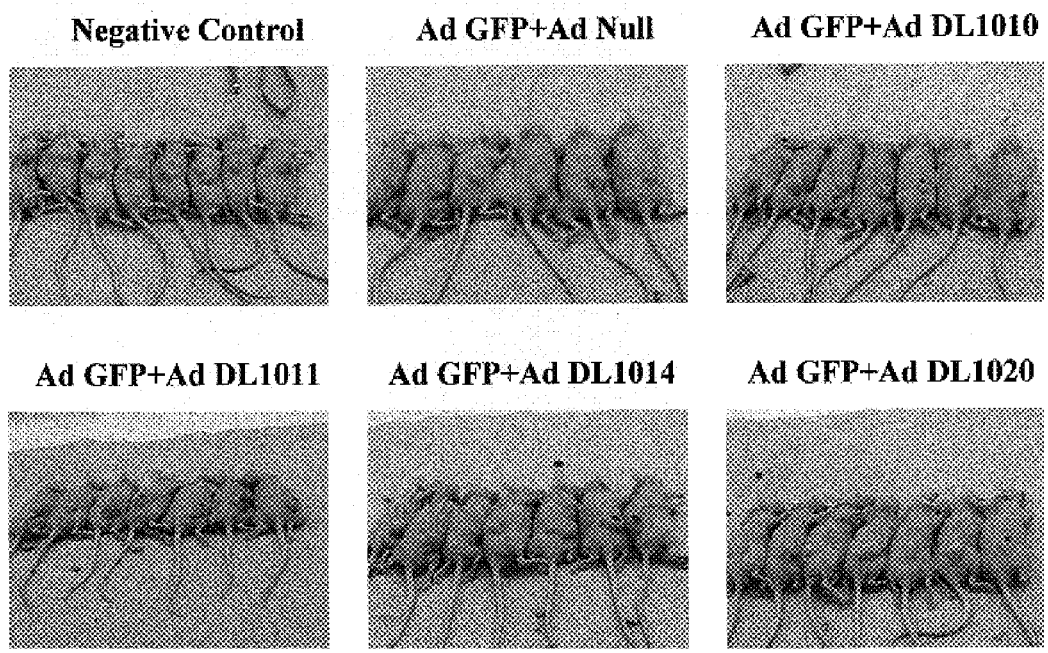

FIG. 14 shows HTC 116 tumors injected $1 \times 10^8$ PFU with ADGFP+Ad Null or AdGFP+Ad dl1011 or AdGFP+Ad dl1010 or AdGFP+Ad dl1014 or Ad GFP+Ad dl1020 and tumors photographed at the indicated times. Again, significant tumor regression is seen with the complementary vector combination.

Figure 15A:
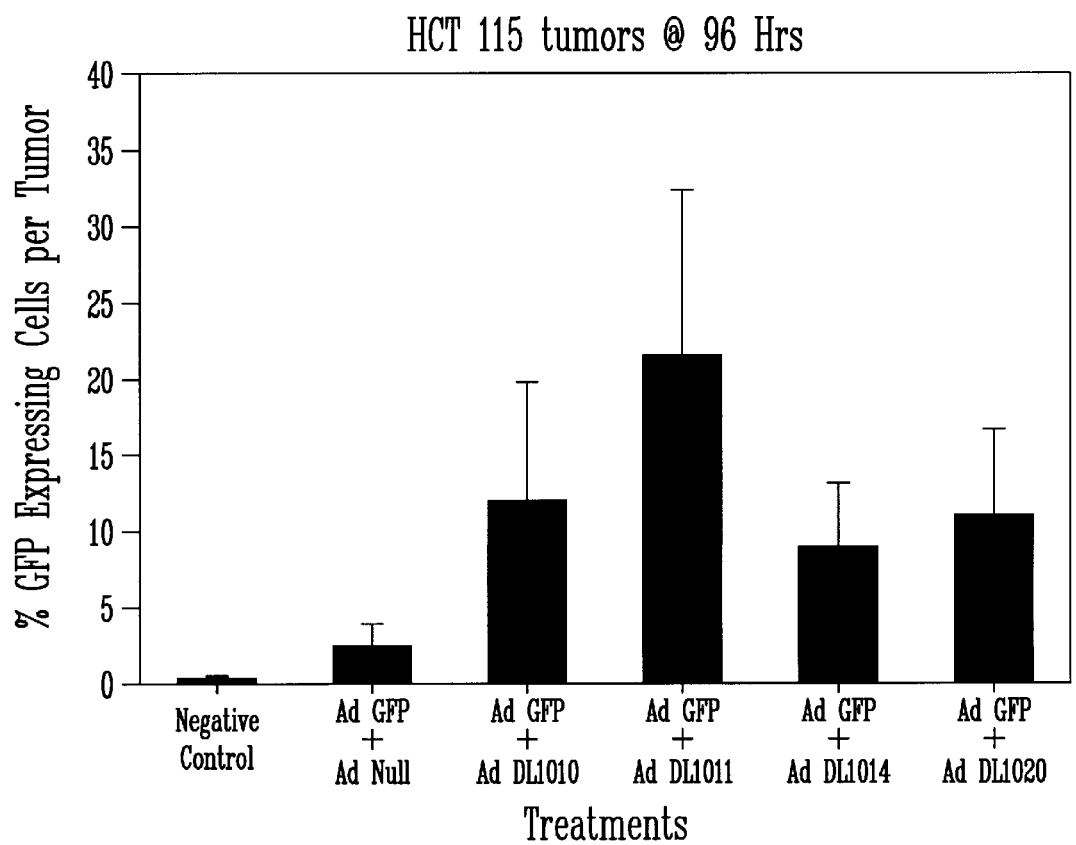
FIGS. 15(a–c) depict HCT 115 tumors were injected 1×10⁸ PFU with Ad GFP+Ad Null or Ad GFP+Ad dl1011 or Ad GFP+Ad dl1010 or Ad GFP+Ad dl1014 or Ad GFP+Ad dl1020 and tumors removed and subjected to FACS at the indicated times.
Figure 15B:
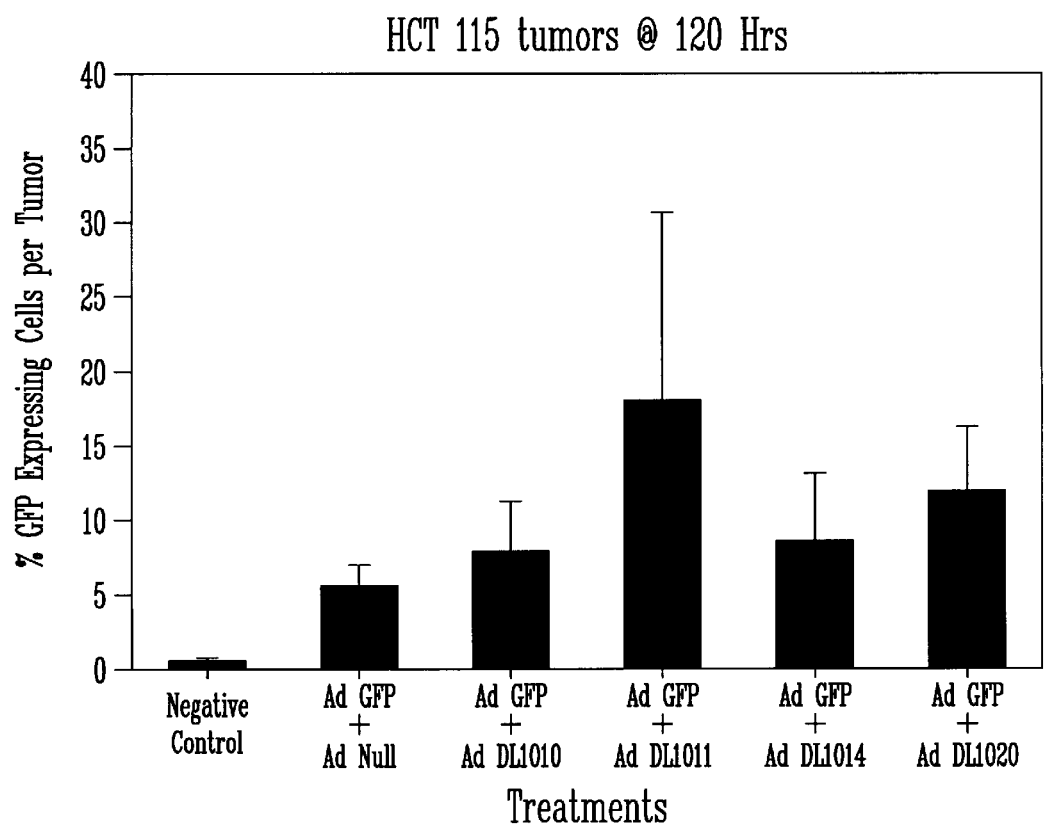
Figure 15C:
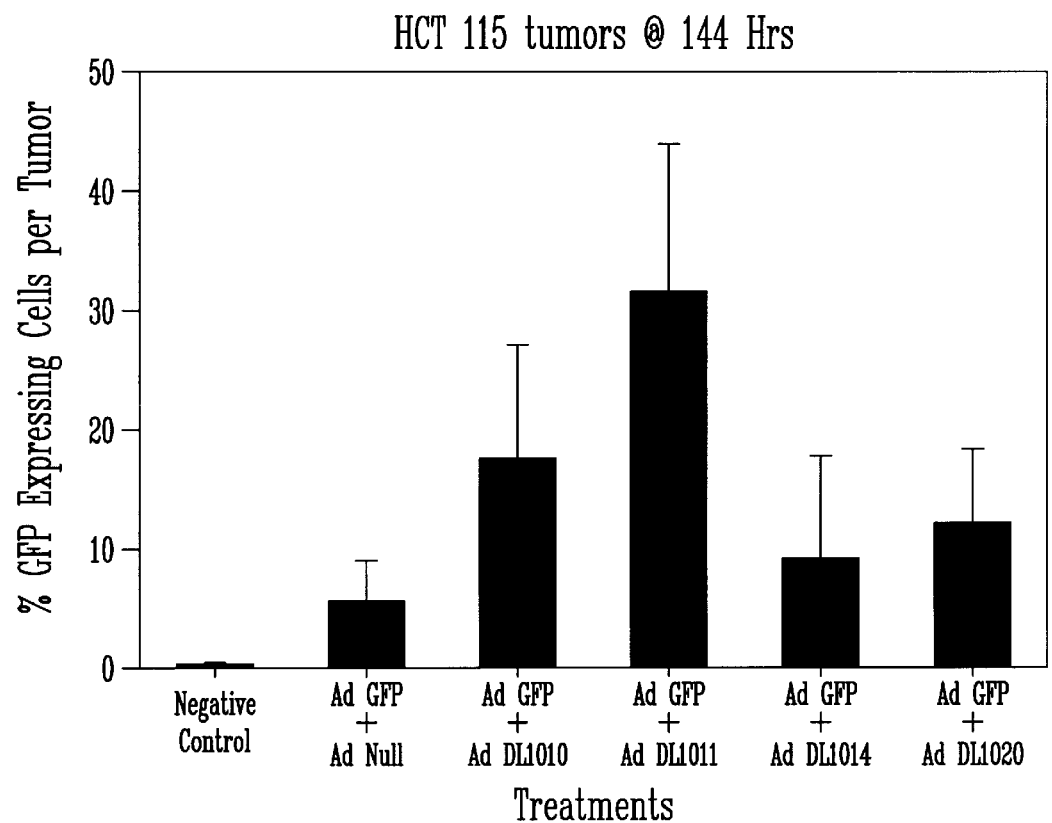

FIGS. 15a–c show graphs of GFP expression. HCT 115 tumors injected into mice. $1 \times 10^8$ PFU with Ad GFP+Ad Null or Ad GFP+Ad i1011 or Ad GFP+Ad dl1010 or Ad GFP+Ad dl1014 or Ad GFP+Ad dl1020 and tumors removed and subjected to FACS at the indicated times.

Figure 16A:
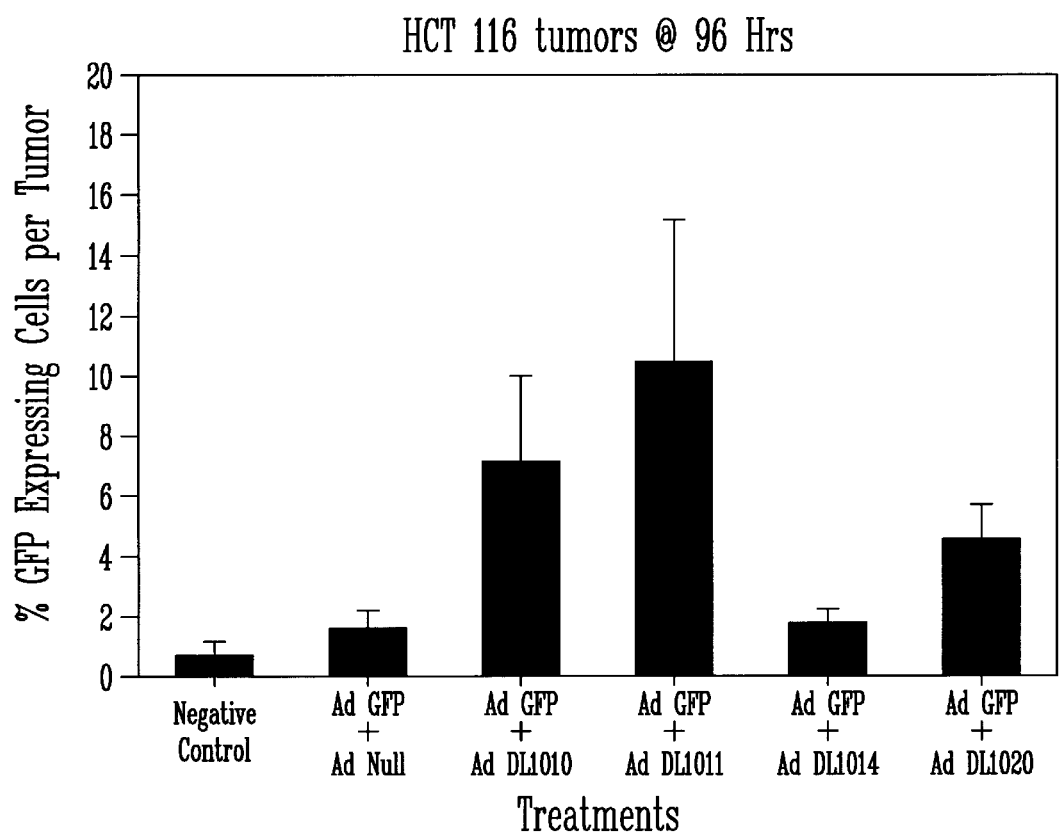
FIGS. 16(a–c) depict HCT 116 tumors were injected 1×10⁸ PFU with Ad GFP+Ad Null or Ad GFP+Ad dl1011 or Ad GFP+Ad dl1010 or Ad GFP+Ad dl1014 or Ad GFP+Ad dl1020 and tumors removed and subjected to FACS at the indicated times.
Figure 16B:
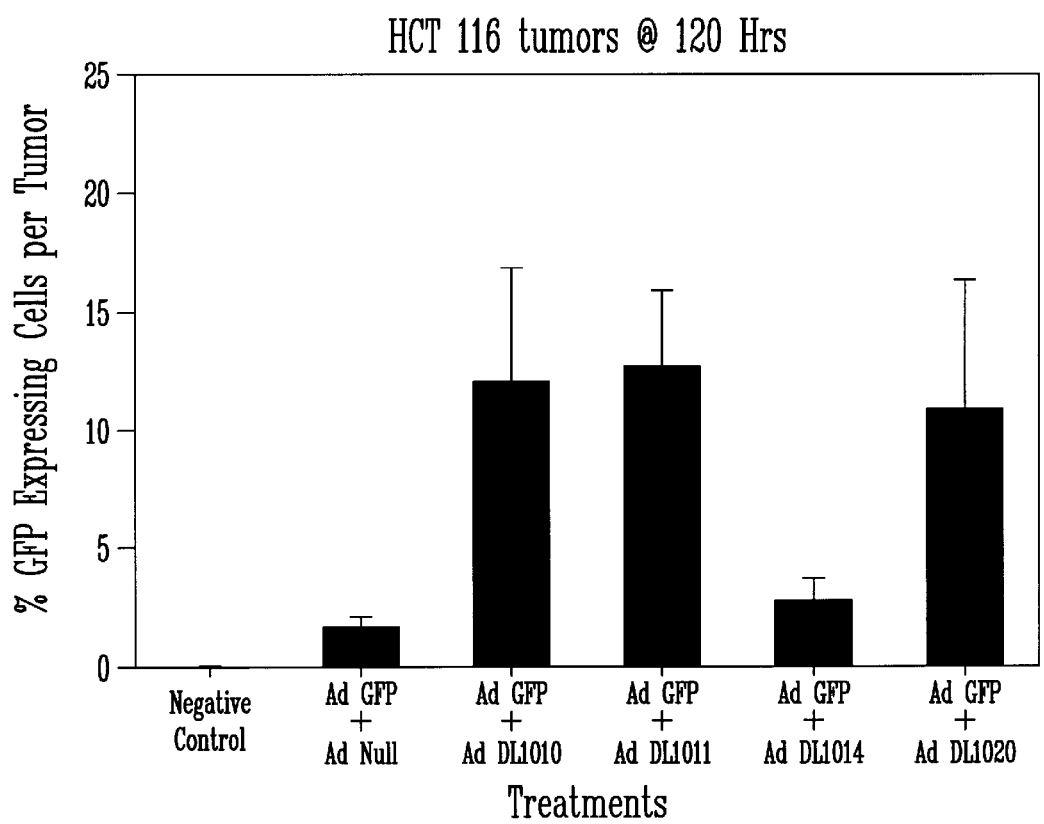
Figure 16C:
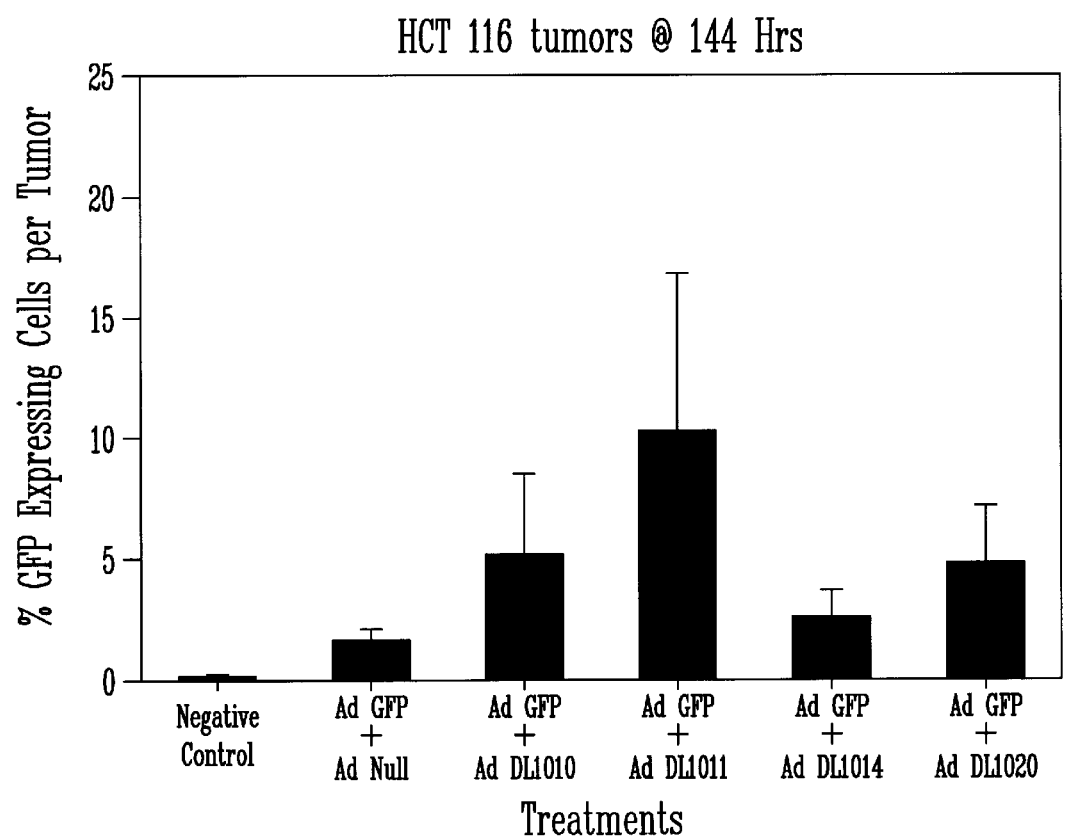

FIGS. 16a–c show graphs of GFP expression. HCT 116 tumors were injected $1 \times 10^8$ PFU with Ad GFP+Ad Null or Ad GFP+Ad dl1011 or Ad GFP+Ad dl1010 or Ad GFP+Ad dl1014 or Ad GFP+Ad dl1020 and tumors removed and subjected to FACS at the indicated times.

Figure 17A:
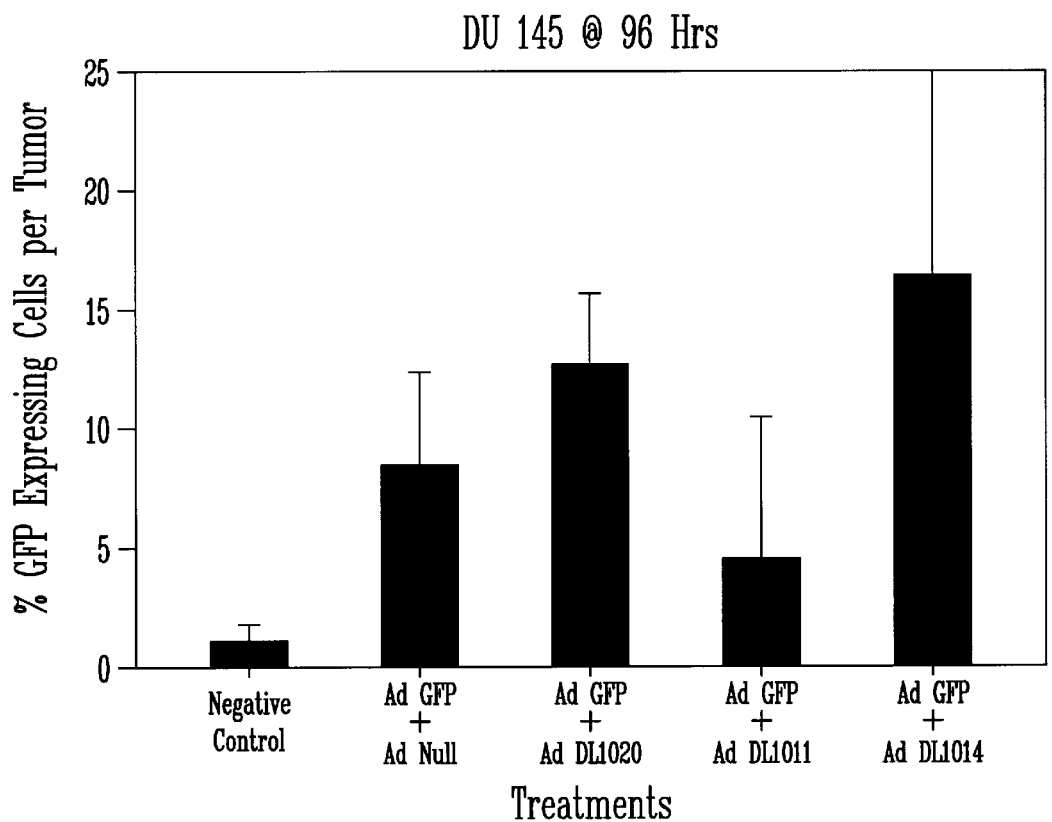
FIGS. 17(a–c) depict DU 145 tumors were injected 1×10⁸ PFU with Ad GFP+Ad Null or Ad GFP+Ad dl1020 or Ad GFP+Ad dl1011 or Ad GFP+Ad dl1014 and tumors removed and subjected to FACS at the indicated times.
Figure 17B:
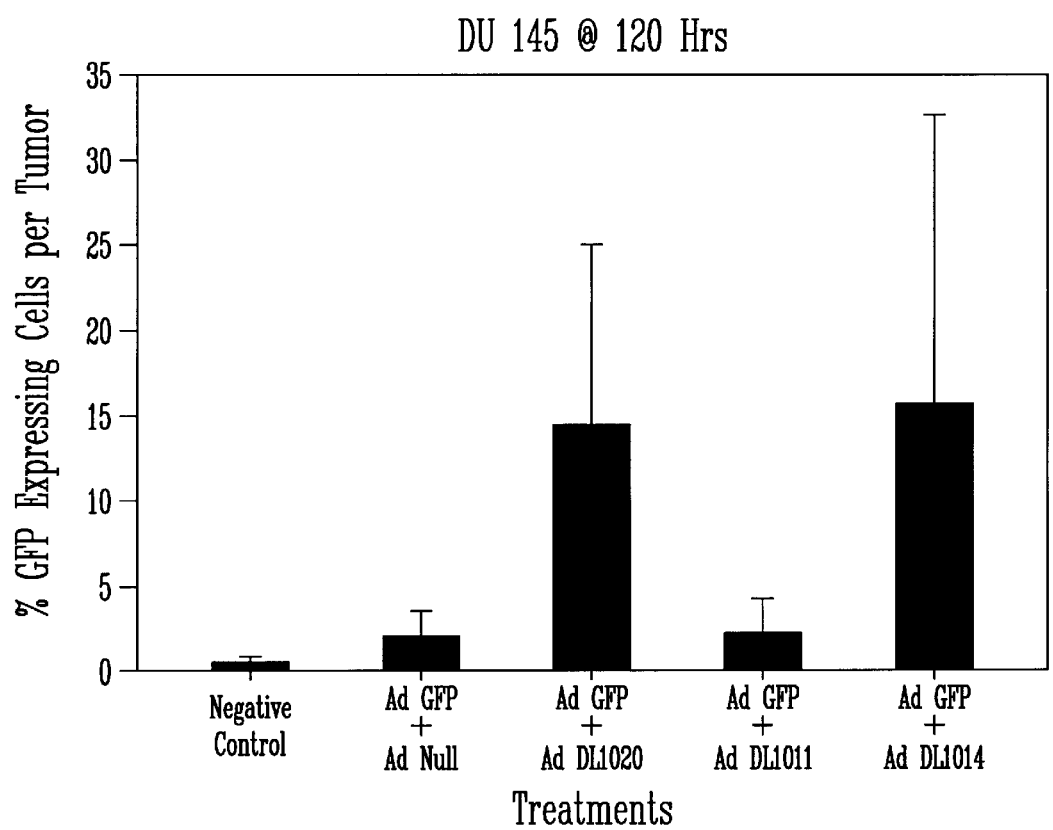
Figure 17C:
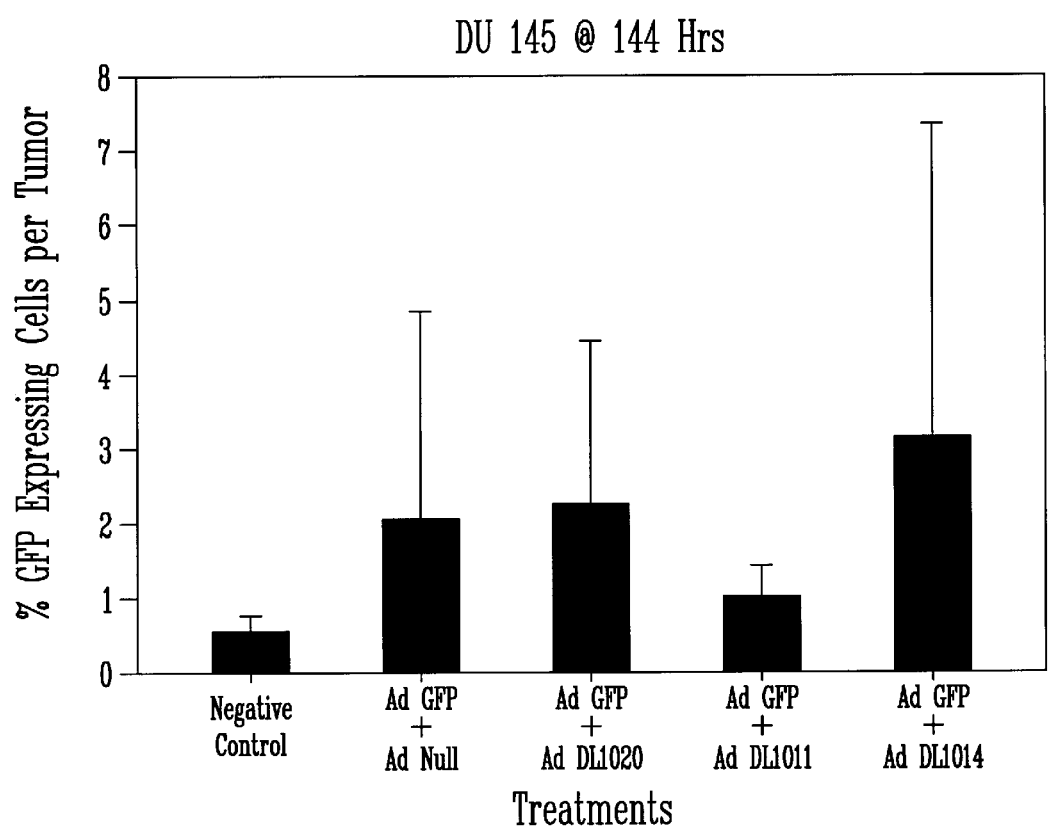

FIGS. 17a–c show graphs of GFP expression. DU 145 tumors were injected $1 \times 10^8$ PFU with Ad GFP+Ad Null or Ad GFP+Ad dl1020 or Ad GFP+Ad dl1011 or Ad GFP+Ad dl1014 and tumors removed and subjected to FACS at the indicated times.

What is claimed is:

1. A method for increasing gene transfer to recipient cells comprising:

introducing to said recipient cell a first replication incompetent adenoviral vector having an E1 deletion, and a second replication incompetent adenoviral vector having an E4 deletion, wherein one or both of said vectors comprise a nucleotide sequence the expression of which is desired in said recipient cell, wherein said first and second adenoviral vectors are transcomplementary, so that upon cotransduction viral replication is enabled, wherein each vector is produced independently of each other in separate trans-complementing packing cell lines.

2. The method of claim 1 wherein said nucleotide sequence is an expression construct.

3. The method of claims 1 wherein one or both of said vectors is an E3 mutant.

4. The method of claim 1 wherein said second vector is recombinant 1014.

5. The method of claim 1 wherein said first vector is AVC2.TK.

6. The method of claim 1 wherein said nucleotide sequence encodes green fluorescent protein.

7. The method of claim 1 wherein said sequence is a tumor suppressor gene.

8. The method of claim 1 wherein said sequence is a tumor suicide gene.

* * * * *